(12) United States Patent
Kusukame et al.

(10) Patent No.: US 8,592,769 B2
(45) Date of Patent: Nov. 26, 2013

(54) COMPONENT CONCENTRATION METER, COMPONENT CONCENTRATION MEASUREMENT METHOD, SHIPPING INSPECTION SYSTEM, AND HEALTH MANAGEMENT SYSTEM

(75) Inventors: Koichi Kusukame, Osaka (JP); Shinichi Kadowaki, Fukuoka (JP); Hiroyuki Furuya, Fukuoka (JP)

(73) Assignee: Panasonic Corporation, Osaka (JP)

( * ) Notice: Subject to any disclaimer, the term of this patent is extended or adjusted under 35 U.S.C. 154(b) by 150 days.

(21) Appl. No.: 13/201,637

(22) PCT Filed: Dec. 10, 2010

(86) PCT No.: PCT/JP2010/007193
§ 371 (c)(1),
(2), (4) Date: Aug. 16, 2011

(87) PCT Pub. No.: WO2011/074217
PCT Pub. Date: Jun. 23, 2011

(65) Prior Publication Data
US 2011/0299066 A1    Dec. 8, 2011

(30) Foreign Application Priority Data

Dec. 18, 2009 (JP) .................................. 2009-287118
Mar. 25, 2010 (JP) .................................. 2010-070765

(51) Int. Cl.
*G01J 5/02* (2006.01)
(52) U.S. Cl.
USPC ..................................................... 250/341.6
(58) Field of Classification Search
USPC ........................ 250/341.6; 600/319
See application file for complete search history.

(56) References Cited

U.S. PATENT DOCUMENTS 5,361,758 A * 11/1994 Hall et al. ............... 600/322
5,383,452 A *  1/1995 Buchert .................. 600/347
(Continued)

FOREIGN PATENT DOCUMENTS

JP    4-208842    7/1992
JP    7-284490    10/1995
(Continued)

OTHER PUBLICATIONS

International Search Report issued Mar. 22, 2011 in International (PCT) Application No. PCT/JP2010/007193.

*Primary Examiner* — David Porta
*Assistant Examiner* — Edwin Gunberg
(74) *Attorney, Agent, or Firm* — Wenderoth, Lind & Ponack, L.L.P.

(57) ABSTRACT

An component concentration meter includes an output unit that outputs an electromagnetic wave to an object to be measured and includes a detecting unit that detects the property of the electromagnetic wave passed through the object to be measured under a first condition and under a second condition in which the temperature of the object to be measured is different from that under the first condition. The component concentration meter also includes a concentration determining unit that determines the concentration of a target component contained in the object to be measured, based on a property difference which is a difference between the properties of the electromagnetic wave detected by the detecting unit under the first condition and under the second condition and a difference between the temperatures of the object to be measured under the first condition and under the second condition.

17 Claims, 22 Drawing Sheets

(56) References Cited

U.S. PATENT DOCUMENTS

| | | | |
|---|---|---|---|
| 5,529,755 A | 6/1996 | Higashio et al. | |
| 5,957,841 A | 9/1999 | Maruo et al. | |
| 6,241,663 B1 | 6/2001 | Wu et al. | |
| 6,424,850 B1 * | 7/2002 | Lambert et al. | 600/319 |
| 6,526,298 B1 | 2/2003 | Khalil et al. | |
| 6,654,620 B2 | 11/2003 | Wu et al. | |
| 6,662,030 B2 | 12/2003 | Khalil et al. | |
| 6,662,031 B1 | 12/2003 | Khalil et al. | |
| 7,043,287 B1 * | 5/2006 | Khalil et al. | 600/310 |
| 2002/0026106 A1 * | 2/2002 | Khalil et al. | 600/310 |
| 2002/0055671 A1 | 5/2002 | Wu et al. | |
| 2004/0101969 A1 * | 5/2004 | Viglianti et al. | 436/173 |
| 2005/0004458 A1 * | 1/2005 | Kanayama et al. | 600/437 |
| 2005/0278002 A1 * | 12/2005 | Eimerl et al. | 607/88 |
| 2007/0218174 A1 | 9/2007 | Hanamatsu et al. | |
| 2009/0105564 A1 * | 4/2009 | Tokita | 600/310 |
| 2009/0204366 A1 * | 8/2009 | Gerlitz | 702/179 |

FOREIGN PATENT DOCUMENTS

| | | |
|---|---|---|
| JP | 10-068692 | 3/1998 |
| JP | 10-325794 | 12/1998 |
| JP | 2003-0502000 | 2/2003 |
| JP | 2003-523793 | 8/2003 |
| JP | 2003-254901 | 9/2003 |
| JP | 2005-292128 | 10/2005 |
| WO | 2007/141859 | 12/2007 |

* cited by examiner

[FIG. 3]
Difference in temperature (°C)
Difference in transmittance (%)

COMPONENT CONCENTRATION METER, COMPONENT CONCENTRATION MEASUREMENT METHOD, SHIPPING INSPECTION SYSTEM, AND HEALTH MANAGEMENT SYSTEM

TECHNICAL FIELD

The present invention relates to a component concentration meter and component concentration measurement method that non-invasively measure the concentration of a target component contained in an object to be measured such as a solid, liquid, or gas, and a shipping inspection system and health management system using that.

BACKGROUND ART

Diabetes is an adult disease such that reduced action of insulin extremely increases the concentration of glucose in the blood (blood sugar level), and is often accompanied by complications such as heart diseases, cerebral infarction, foot gangrene, and blindness caused by retinal detachment. The Ministry of Health, Labour and Welfare survey of diabetes in 2002 reports that approximately 7.4 million people in Japan are "strongly suspected of" diabetes, and the number of the potential diabetics "who may have diabetes" amounts to approximately 16.2 million, which corresponds to one adult per 6.3 adults. In the future, further increase in the number of the diabetes is expected not only in Japan but also in the world. Usually, it is difficult to become aware of diabetes until the concentration of glucose is extremely increased or serious complications are demonstrated. Accordingly, a periodical diagnosis at an early stage including a blood test is particularly important for prevention of the diabetes.

Usually, the blood test is performed in order to monitor a blood sugar level in the blood in real time. For this, a skin of a person to be tested needs to be pierced by a needle to extract the blood. Such extraction of the blood, however, gives much pain to the person to be tested, and includes a risk that the person to be tested may be infected with various infectious diseases unless the needle is treated safely.

For this, establishment of a non-invasive method for accurately measuring the concentration of glucose in the blood without extracting the blood has been strongly desired.

Several non-invasive methods for measuring the blood sugar level have been proposed. For example, a method has been proposed in which the concentration of glucose in an object to be measured is determined using near-infrared spectroscopic analysis (Patent Literature 1). In the method, near-infrared radiation is projected onto the skin of a person to be tested, and the emitted light from the skin is received by an optical fiber bundle.

The spectrum of the emitted light by the optical fiber bundle is analyzed to detect absorption signals from a first wavelength band having an absorption peak of an OH group derived from the glucose molecules (for example, 1550 to 1650 nm), a second wavelength band having an absorption peak of an NH group derived from the glucose molecules (for example, 1480 to 1550 nm), and a third wavelength band having an absorption peak of a CH group derived from the glucose molecules (for example, 1650 to 1880 nm). The concentration of glucose is determined by multivariate analysis based on these absorption signals.

Moreover, a method has been proposed in which the concentration of a target component in a medium is determined based on a probability and statistics simulation (Patent Literature 2). In the method, a group of optical paths in the medium is analyzed by the probability and statistics simulation such as a Monte Carlo method. A database is created, which shows an absorption coefficient as an optical property of the medium and change of diffusion reflectance in the case where an equivalent diffusion coefficient is changed within a predetermined range thereof. Next, the diffusion reflectance is smoothed by a method of regression analysis to create a correction database. Next, the medium is irradiated with near-infrared light in the wavelength band of 1000 to 2500 nm to detect the emitted light from the medium, and the thus-obtained measured spectrum is compared with the reference spectrum provided by the correction database to determine the concentration of the target component in the medium. According to the method, if the change in the spectrum caused by change in the concentration of the component other than the target component in the medium is computed from the correction database, the concentration of the target component can be determined from the measured spectrum by the multivariate analysis such as principal components regression (PCR) and multiple regresssion analysis (MLR).

CITATION LIST

Patent Literature

[PTL 1] Japanese Unexamined Patent Application Publication No. 10-325794

[PTL 2] Japanese Unexamined Patent Application Publication No. 2003-50200

SUMMARY OF INVENTION

Technical Problem

According to the conventional blood sugar level measuring apparatus as shown in Patent Literatures 1 and 2, however, the absorption signal of the target component such as glucose is sensitive to the concentration of other component such as water, lipid, and protein. For this reason, it is difficult to accurately analyze the target component using the peak position and peak height in the absorption signal.

The present invention has been made considering the problem, and an object of the present invention is to provide non-invasive (non-destructive) measurement by a component concentration meter and a component concentration measurement method in which the concentration of the target component contained in an object to be measured is accurately measured.

Solution to Problem

A component concentration meter according to one embodiment of the present invention includes an output unit configured to output an electromagnetic wave to the object to be measured; a detecting unit configured to detect a property of the electromagnetic wave passed through the object to be measured under a first condition and under a second condition in which the temperature of the object to be measured is different; and a concentration determining unit configured to determine the concentration of the target component contained in the object to be measured, based on a property difference which is a difference between the properties of the electromagnetic wave detected by the detecting unit under the first condition and under the second condition, and a difference between the temperatures of the object to be measured under the first condition and under the second condition.

As the configuration above, the concentration is measured using the difference in the temperature of the object to be measured and the property difference of the electromagnetic wave passed through the object to be measured. Thereby, the influence of the component other than the target component contained in the object to be measured can be eliminated. As a result, accuracy in the measurement is improved. Moreover, the object to be measured is only irradiated with the electromagnetic wave, and thus a non-invasive measurement can be achieved.

The detecting unit may be configured to detect a property of a electromagnetic wave passed through the object to be measured under a first condition in which a first electromagnetic wave pulse is output from the output unit and under a second condition in which a second electromagnetic wave pulse having a different pulse energy from the pulse energy of the first electromagnetic wave pulse is output from the output unit.

As an example, the output unit may be configured to output the first and second electromagnetic wave pulses each having a different pulse energy by varying a peak power between the first and second electromagnetic wave pulses.

As other example, the output unit may be configured to output the first and second electromagnetic wave pulses each having a different pulse energy by varying an irradiation time with the electromagnetic wave pulse between the first and second electromagnetic wave pulses.

Irradiation with an electromagnetic wave pulse having a large pulse energy sharply increases the temperature of the object to be measured. On the other hand, irradiation with an electromagnetic wave pulse having a small pulse energy mildly increases the temperature of the object to be measured. Thus, irradiation with an electromagnetic wave pulse having a different pulse energy can provide the first and second conditions each having a different temperature.

The output unit may be configured to output an electromagnetic wave for detection that has a first wavelength and passes through the object to be measured to be detected by the detecting unit and an electromagnetic wave for heating that has a second wavelength and is absorbed by the object to be measured to increase the temperature of the object to be measured. Desirably, the electromagnetic wave for detection has a property that significantly changes according to change of the temperature of the object to be measured compared to the electromagnetic wave for heating, and the electromagnetic wave for heating has an absorption by the object to be measured larger than an absorption of the electromagnetic wave for detection.

Thereby, a wavelength (first wavelength) suitable for detection and a wavelength (second wavelength) suitable for heating can be properly selected according to the target component. As a result, accuracy in the measurement is improved.

As an example, in the case where the target component is glucose, the output unit is desirably configured to output the electromagnetic wave for detection having the first wavelength selected from the range of not less than 1600 nm and not more than 1900 nm, the range of not less than 900 nm and not more than 1050 nm, or the range of not less than 1200 nm and not more than 1270 nm.

As other example, in the case where the object to be measured contains moisture, the output unit is desirably configured to output the electromagnetic wave for detection having the first wavelength selected from the range of not less than 1100 nm and not more than 1180 nm or the range of not less than 900 nm and not more than 990 nm.

As still other example, in the case where the object to be measured includes a biological cell, the output unit is desirably configured to output an electromagnetic wave for heating having a pulse width of not less than 10 ns and not more than 1 µs.

In the case where the object to be measured is an anterior aqueous humor in an eye, the component concentration meter may further include a cylindrical body having a bottom and an opening on a top surface of the cylindrical body, and holding a protection solution having a higher refractive index than a refractive index of the anterior aqueous humor in an eye within the cylindrical body having a bottom, wherein the output unit is provided on the side surface of the cylindrical body having a bottom so as to output an electromagnetic wave passing through the protection solution to the opening, and the detecting unit is provided on the side surface of the cylindrical body having a bottom so as to detect a property of the electromagnetic wave that enters from the opening and passes through the protection solution.

According to the configuration above, the opening of the cylindrical body having a bottom is pressed against the eye for measurement to increase the angle of incidence of the electromagnetic wave with which the eye is irradiated. As a result, the reflectance of the electromagnetic wave is improved, and an electromagnetic wave having a large output can be detected by the detecting unit.

The surface of the cylindrical body having a bottom may be light-shielded. Thereby, the pupil is opened wider during the measurement, which facilitates the measurement.

The component concentration meter may further include an electromagnetic wave converging unit configured to converge the electromagnetic wave output from the output unit, and provided in an electromagnetic wave propagation path between the output unit and the object to be measured. Thereby, the object to be measured can be locally heated. Accordingly, the temperature of the object to be measured can be efficiently increased with a small output.

The component concentration meter may further include a storing unit configured to store an association table that holds the property difference, the difference in the temperature, and the concentration of the target component in association, wherein the concentration determining unit is configured to determine the concentration of the target component corresponding to the property difference and the difference in the temperature detected by the detecting unit with reference to the association table held in the storing unit. Alternatively, the storing unit may store an equation using the property difference, the difference in the temperature, and the concentration as parameters.

The component concentration meter may further include a smoothing material that smoothes depressions and projections of the object to be measured in order to provide a uniform distribution of intensity of an electromagnetic wave in a propagation path from the output unit to the detecting unit. This can suppress change in distribution of the intensity of the electromagnetic wave by the depressions and projections of the object to be measured, thereby improving the accuracy of the measurement.

The component concentration meter may include a polarized wave separating unit configured to extract a predetermined polarization component contained in the electromagnetic wave passed through the object to be measured, wherein the detecting unit is configured to detect a degree of optical rotation of the polarization component extracted by the polarized wave separating unit under the first condition and under the second condition, and the concentration determining unit is configured to determine the concentration of the target component contained in the object to be measured, based on the difference in the temperature and the difference in the degree of optical rotation. Here, the "degree of optical rotation" is an example of the property of the electromagnetic wave. Other than this, the property such as transmittance of the electromagnetic wave and circular dichroism may be used.

The output unit may be configured to output an electromagnetic wave having a first wavelength and an electromagnetic wave having a second wavelength. The component concentration meter may further include a synthesizing unit configured to synthesize the electromagnetic wave having the first wavelength with the electromagnetic wave having the second wavelength and output the synthesized electromagnetic wave to the object to be measured; and a separating unit configured to separate an electromagnetic wave passed through the object to be measured into the electromagnetic wave having the first wavelength and the electromagnetic wave having the second wavelength.

The output unit includes an oscillating unit configured to oscillate an electromagnetic wave having a first wavelength; and a wavelength converting unit configured to convert part of the electromagnetic wave oscillated by the oscillating unit into an electromagnetic wave having a second wavelength different from the first wavelength.

According to each of the configurations above, the electromagnetic wave having the first wavelength and that having the second wavelength are easily overlaid on the same propagation path. As the electromagnetic wave having the first wavelength and that is having the second wavelength, one of them may be used as the electromagnetic wave for detection, and the other may be used as the electromagnetic wave for heating. Alternatively, in the case where circular dichroism or the like is detected, both of them may be used as the electromagnetic wave for detection.

A component concentration measurement method according to one embodiment of the present invention includes outputting an electromagnetic wave to the object to be measured, detecting a property of the electromagnetic wave passed through the object to be measured under a first condition and under a second condition in which the temperature of the object to be measured is different, and determining the concentration of the target component contained in the object to be measured, based on a property difference which is a difference between the properties of the electromagnetic wave detected in the detecting under the first condition and under the second condition, and a difference between the temperatures of the object to be measured under the first condition and under the second condition.

An shipping inspection system according to one embodiment of the present invention includes the component concentration meter above; and a conveyor configured to sequentially convey a plurality of objects to be measured to a measurement position for the component concentration meter.

A health management system according to one embodiment of the present invention includes the component concentration meter above configured to calculate a concentration of each of the components contained in the object to be measured, and a calorie calculating unit configured to calculate a calorie of the object to be measured, based on the concentration of each of the components calculated by the component concentration meter.

A health management system according to other embodiment of the present invention includes the component concentration meter above configured to calculate a concentration of each of the several kinds of saccharides contained in the object to be measured, and a sweetness calculating unit configured to calculate sweetness of the object to be measured, based on the concentration of each of the several kinds of saccharides calculated by the component concentration meter.

The present invention can be implemented not only as the component concentration meter and the component concentration measurement method, but also as a program enabling a computer to execute the steps included in the component concentration measurement method, or as a semiconductor integrated circuit (LSI) that implements some of the functions of the component concentration meter. Moreover, the program can be distributed through a non-temporary computer readable recording medium such as a CD-ROM and a transmitting medium such as the Internet.

Advantageous Effects of Invention

The component concentration meter according to the present invention can non-invasively (non-destructively) determine the concentration of the target component contained in an object to be measured with higher accuracy.

DESCRIPTION OF EMBODIMENTS

As a result of original research in order to solve the problem, the inventors found out that in the electromagnetic waves at several wavelengths, the absorptivity (transmittance) of glucose changes depending on the temperature thereof. The transmittance of glucose (crystal length of 1 cm) whose temperature is varied is measured using a spectrophotometer, and the result is shown below.

Figure 21:
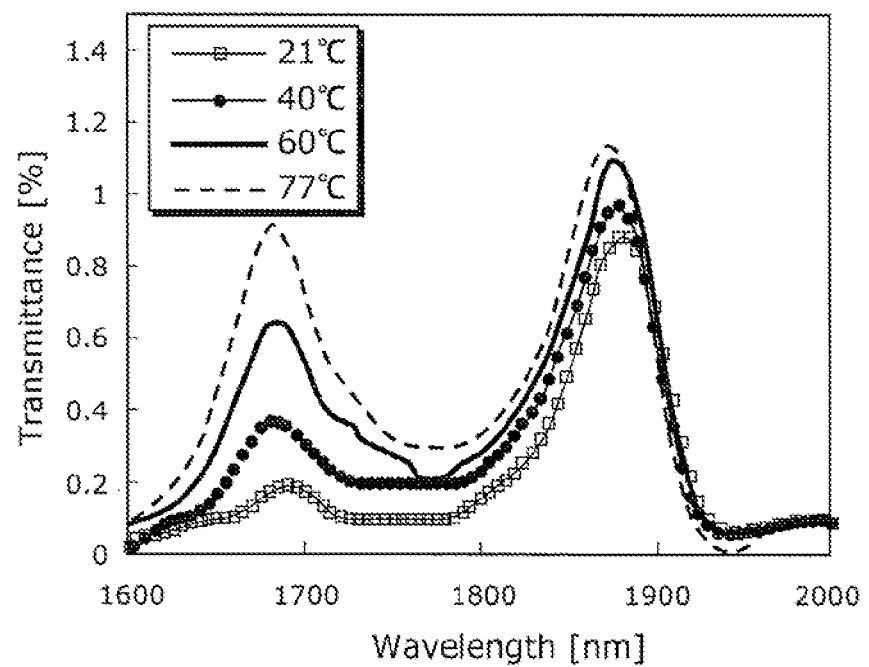
FIG. 21 is a drawing showing a relationship between the temperature and transmittance of glucose in the case of near-infrared light having a wavelength of not less than 1600 nm and not more than 2000 nm.

First, the near-infrared light having a wavelength of not less than 1600 nm and not more than 2000 nm enters glucose. A graph showing the relationship between the transmittance and the temperature is shown in FIG. 21. With reference to FIG. 21, it turns out that the higher the temperature becomes, the higher the transmittance becomes in the case of the near-infrared light having a wavelength in the range of not less than 1600 nm and not more than 1900 nm.

Figure 22:
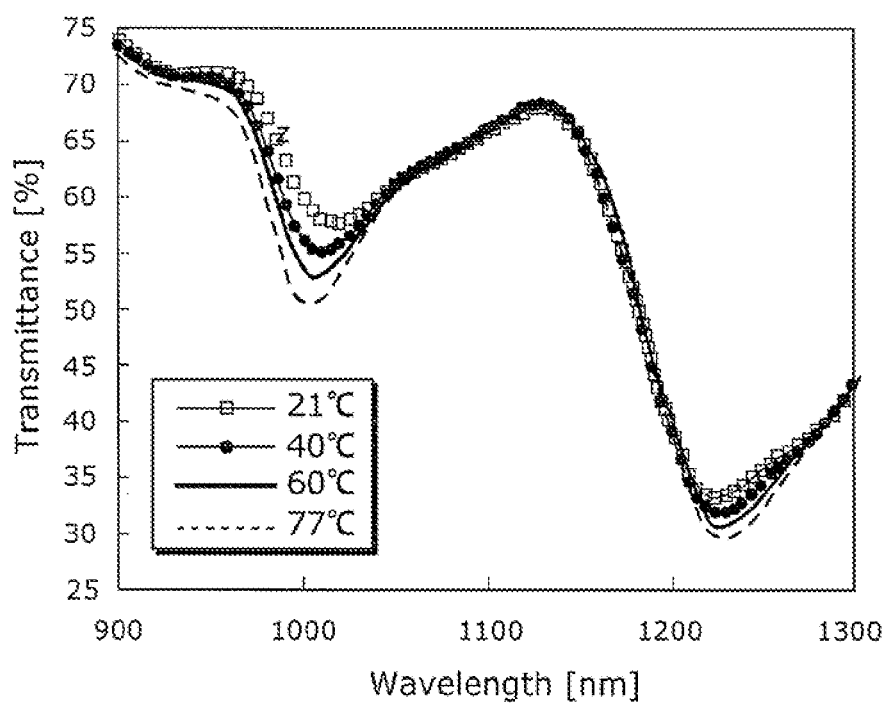
FIG. 22 is a drawing showing a relationship between the temperature and transmittance of glucose in the case of near-infrared light having a wavelength of not less than 900 nm and not more than 1300 nm.

Moreover, the near-infrared light having a wavelength in the range of not less than 900 nm and not more than 1300 nm enters glucose. A graph showing the relationship between the transmittance and the temperature is shown in FIG. 22. With reference to FIG. 22, it turns out that the higher the temperature becomes, the lower the transmittance becomes in the case of the near-infrared light having a wavelength in the range of not less than 900 nm and not more than 1050 nm and in the range of not less than 1200 nm and not more than 1270 nm.

Similarly, it turns out that in a mixture containing glucose, the transmittance depends on the temperature. It also turns out that when the temperature of the mixture is changed, the amount of the transmittance to be changed is proportional to the concentration of glucose.

Figure 23:
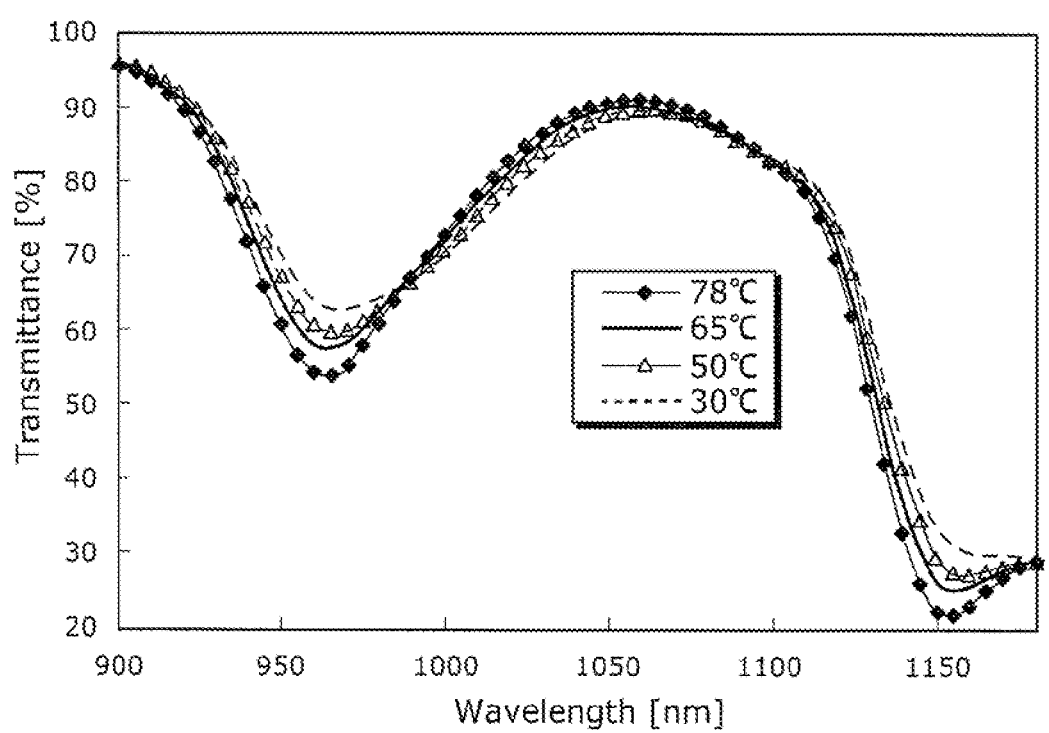
FIG. 23 is a drawing showing a relationship between the temperature and transmittance of glucose in the case of near-infrared light having a wavelength of not less than 900 nm and not more than 1180 nm.

Moreover, the relationship between the transmittance and the temperature was also examined in a substance other than glucose. The near-infrared light having a wavelength in the range of not less than 900 nm and not more than 1180 nm enters distilled water (cell length of 1 cm). The relationship between the transmittance and the temperature is determined, and the result is shown in FIG. 23. With reference to FIG. 23, in the case of water, it turns out that the higher the temperature becomes, the lower the transmittance becomes in the case of the near-infrared light having a wavelength in the range of not less than 1100 nm and not more than 1180 nm and in the range of not less than 900 nm and not more than 990 nm.

In the component concentration meter according to one embodiment of the present invention, an environmental change such as change in the temperature (change in temperature, pressure, intensity of the light, or an electric field) is given to the target component, and the concentration of the target component is determined from the amount of an optical property (such as transmittance and optical rotation) to be changed accompanied by the environmental change. Thereby, the concentration of the target component can be measured with higher accuracy than in the conventional method.

Hereinafter, a component concentration meter according to one embodiment of the present invention will be described with reference to the drawings.

Here, the visible light and ultraviolet light having a wavelength of several hundreds nm or less to the microwave at a wavelength of several tens mm or more (frequency of several GHz or less) are generally written as an "electromagnetic wave" and described. Polarization of the light and polarization of the electromagnetic wave are generally written as "polarization" and described. A light source in the light and an oscillating unit in the electromagnetic wave are generally written as an "oscillating unit" and described. An optical path of the light and a propagation path of the electromagnetic wave are generally written as a "propagation path" and describes.

Figure 1:
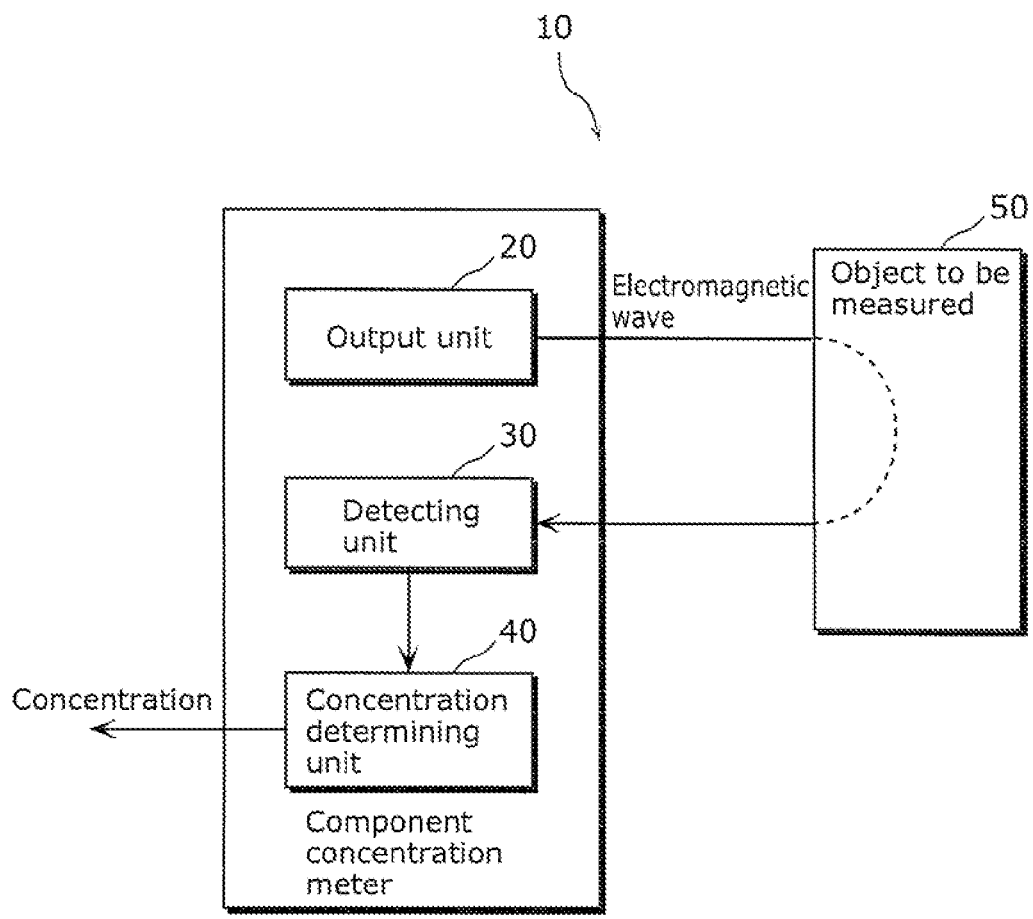
FIG. 1 is a block diagram of a schematic configuration of a component concentration meter according to one embodiment of the present invention.
Figures 2, 3:
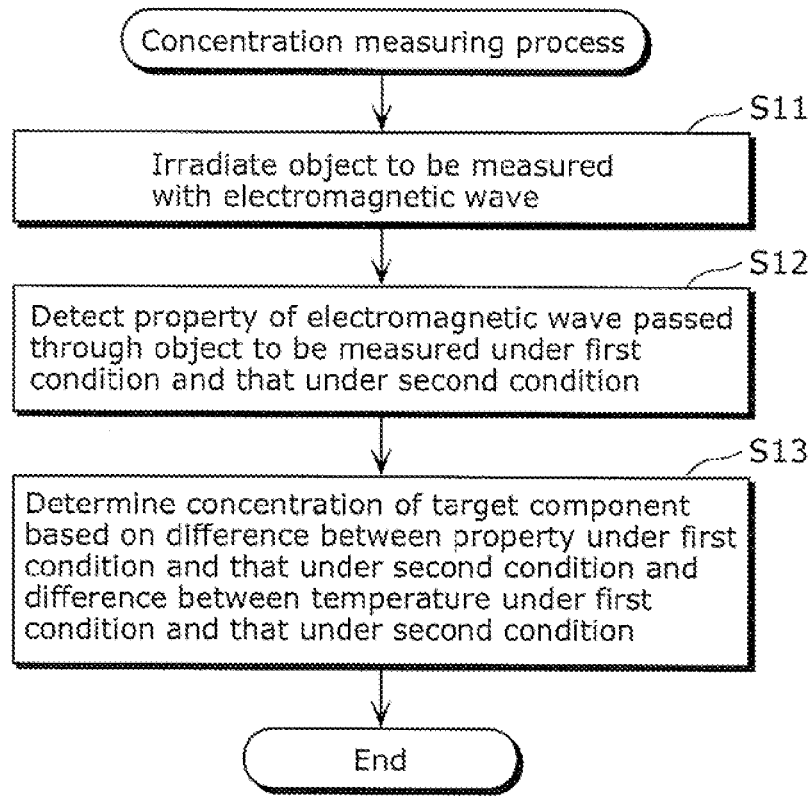
FIG. 2 is a flowchart showing a component concentration measurement method according to one embodiment of the present invention.
FIG. 3 is a drawing showing an example of a table used in a component concentration measurement method.

First, with reference to FIGS. 1 to 3, a component concentration meter 10 and a component concentration measurement method according to one embodiment of the present invention will be described. FIG. 1 is a block diagram of a schematic configuration showing the component concentration meter 10. FIG. 2 is a flowchart of a component concentration measurement method. FIG. 3 shows a table used in the component concentration measurement method.

As shown in FIG. 1, the component concentration meter 10 includes an output unit 20, a detecting unit 30, and a concentration determining unit 40, and measures the concentration of a target component contained in an object to be measured 50.

The output unit 20 outputs an electromagnetic wave to the object to be measured 50. The wavelength of the electromagnetic wave to be output from the output unit 20 is selected according to the target component contained in the object to be measured 50.

The detecting unit 30 detects the property of the electromagnetic wave output from the output unit 20 and passed through the object to be measured 50. More specifically, the detecting unit 30 detects the property of the electromagnetic wave under a first condition and under a second condition. Here, the first and second conditions are the conditions in which at least the temperature of the object to be measured 50 is different. Examples of the properties of the electromagnetic wave include the transmittance, the degree of optical rotation, and circular dichroism.

The concentration determining unit 40 determines the concentration of the target component contained in the object to be measured 50, based on a property difference which is the difference between the properties of the electromagnetic wave detected by the detecting unit 30 under the first condition and under the second condition, and a difference in the temperature of the object to be measured 50 under the first condition and under the second condition.

The thus-configured component concentration meter 10 measures the concentration of the target component contained in the object to be measured 50 according to the procedure as shown in FIG. 2, for example. First, the output unit 20 outputs the electromagnetic wave to the object to be measured 50 (S11).

Next, the detecting unit 30 detects the property of the electromagnetic wave passed through the object to be measured 50 several times (typically, twice) (S12). The temperature of the object to be measured 50 is gradually increased during irradiation with the electromagnetic wave. Accordingly, the detecting unit 30 detects the property of the electromagnetic wave twice at different times, for example. Thereby, the properties of the electromagnetic wave under different conditions each can be detected.

Next, the concentration determining unit 40 calculates the difference between the properties detected by the detecting unit 30 twice (property difference) and a difference between the temperatures of the object to be measured 50 at the times of detection (difference in the temperature). Then, using the table shown in FIG. 3, the concentration determining unit 40 determines the concentration of the target component corresponding to the calculated property difference and difference in the temperature (S13).

The table shown in FIG. 3 holds the property difference (in the example of FIG. 3, the difference in the transmittance), the difference in the temperature, and the concentration of the target component in association. The table is stored in a storing unit (illustration is omitted) in the component concentration meter 10, for example. The relationship among the difference in the property, the difference in the temperature, and the concentration held by the table is calculated in advance by an examination or the like.

The example of FIG. 3 is the result when the light having a wavelength of 1670 nm enters the object to be measured (length of the optical path in the object to be measured is 1 cm) containing glucose, and the transmittance is measured while the temperature of the object to be measured is changed. Here, supposing that in other component than glucose in the object to be measured, the absorptivity of the light having a wavelength of 1670 nm is not changed even if the temperature is changed, a positive correlation is found between the concentration of glucose (mass percent concentration of glucose) and the amount of the temperature of change in the object to be measured, as shown in FIG. 3.

Instead of the table shown in FIG. 3, the corresponding relationship may be held by an equation using the property difference, the difference in the temperature, and the concentration as parameters. Namely, the equation may be prepared in advance, into which two of the difference in the property, the difference in the temperature, and the concentration are substituted to determine the other one. Alternatively, instead of the concentration, the corresponding relationship among the difference in the property, the difference in the temperature, and the amount (mass) of the component may be held.

According to the method, the concentration of the target component contained in the object to be measured 50 can be non-invasively measured with high accuracy. Hereinafter, with reference to Embodiments 1 to 8, the component concentration meter according to one embodiment of the present invention will be described in detail.

Embodiment 1

Figure 4:
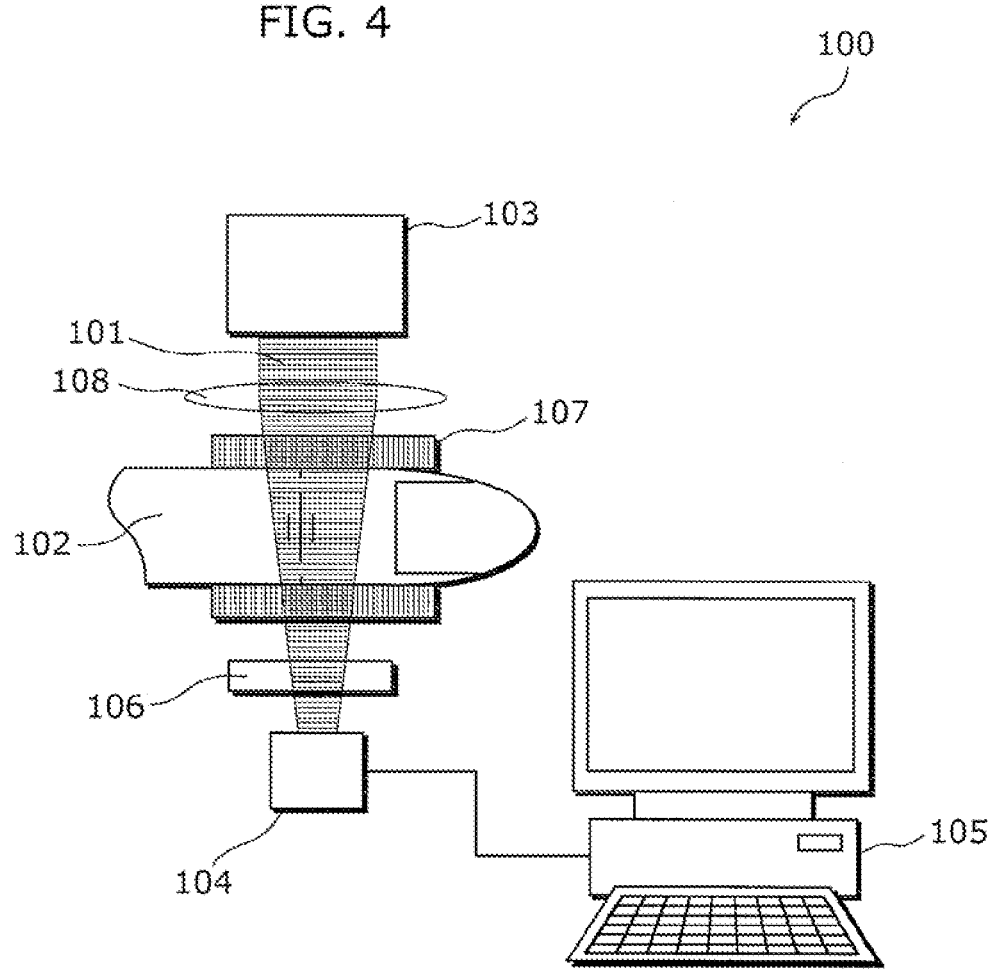
FIG. 4 is a drawing showing a schematic configuration of a component concentration meter according to Embodiment 1 of the present invention.

FIG. 4 is a drawing showing a schematic configuration of a component concentration meter 100 according to Embodiment 1 of the present invention.

In the present embodiment, the component concentration meter 100 that measures the concentration of glucose contained in the blood vessel of a finger as an example of the object to be measured 102 will be described.

As shown in FIG. 4, the component concentration meter 100 according to the present embodiment includes an oscillating unit 103 configured to oscillate an electromagnetic wave 101 to the object to be measured 102, a detecting unit 104 configured to detect the electromagnetic wave 101 passed through the object to be measured 102, a computing unit 105 configured to calculate the concentration of the target component contained in the object to be measured 102 (in the example, glucose) based on the detection result in the detecting unit 104, a filter 106, a depression projection smoothing material 107, and a converging lens 108. The oscillating unit 103 corresponds to the output unit 20 in FIG. 1, the detecting unit 104 to the detecting unit 30 in FIG. 1, and the computing unit 105 to the concentration determining unit 40 in FIG. 1, respectively.

Here, the electromagnetic wave 101 needs to include at least a wavelength that is absorbed by the object to be measured 102. In the present embodiment, the electromagnetic wave 101 includes the near-infrared light having a wavelength in the range of not less than 1600 nm and not more than 1900 nm. As the oscillating unit 103, a halogen light source, the infrared LED, a super luminescent diode, and a laser light source such as a semiconductor laser and a super continuum light source using a mode-locked semiconductor laser as an excitation light source may be used, for example. The laser light source is compact, and can produce the light having high intensity, enabling reduction in the size of the apparatus and measurement with higher accuracy.

As the detecting unit 104, an InGaAs material or an HgCdTe material is used, for example. Moreover, use of a light receiving element having a quantum well structure enables the measurement with higher sensitivity in the wavelength band of the near-infrared light from 1000 nm to 2500 nm. Use of the electromagnetic wave in the wavelength band for detection enables the measurement with higher accuracy.

In the present embodiment, the oscillating unit 103 is modulated and driven to turn ON or OFF the electromagnetic wave (in the drawing, written as "electromagnetic wave input." The same is true hereinafter.) to be input to the object to be measured 102, as shown in FIG. 5(a). Thereby, as shown in FIG. 5(b), the object to be measured 102 absorbs part of the electromagnetic wave during irradiation with the electromagnetic wave. As a result, the temperature of the object to be measured 102 is increased over time. On the other hand, the temperature of the object to be measured 102 is reduced over time during a period of time when the object to be measured 102 is not irradiated with the electromagnetic wave. Here, the power of the electromagnetic wave during irradiation with the electromagnetic wave is constant.

Thus, if the temperature of the object to be measured 102 changes, the absorptivity of the near-infrared light (wavelength of not less than 1600 nm and not more than 1900 nm) absorbed by glucose changes. For this reason, the electromagnetic wave to be output from the object to be measured 102 (in the drawing, written as "electromagnetic wave output." The same is true hereinafter.), namely; the electromagnetic wave to be detected by the detecting unit 104 changes with the time, as shown in FIG. 5(c).

In this state, using the computing unit 105, a transmittance (electromagnetic wave detected by the detecting unit 104/ electromagnetic wave oscillated by the oscillating unit 103) at a point A (measurement time A: immediately after irradiation with the electromagnetic wave is started) in FIG. 5(c), and that at a point B (measurement time B: immediately before irradiation with the electromagnetic wave is stopped) each are measured to determine the difference (the amount of change). The amount of the transmittance to be changed depends on the amount of glucose in the electromagnetic wave propagation path and the amount of change in the temperature of the object to be measured 102. Accordingly, the amount of glucose can be determined by determining the amount of the temperature to be changed between the point A and the point B.

The amounts of other components than glucose, which are needed in order to calculate the concentration of glucose, can be determined in the same manner as in the conventional method as follows: the object to be measured 102 is irradiated with the electromagnetic wave at a plurality of wavelengths, and the amounts of the other components are determined from the transmittances of the respective wavelengths by the multivariate analysis.

Desirably, similarly to the case of glucose, the other components than glucose are determined from the amount of change in the transmittance of the electromagnetic wave at a specific wavelength at which the absorptivity changes according to the change in the temperature. Thereby, the other components than glucose can be measured with higher accuracy, therefore leading to calculation of the concentration of glucose with higher accuracy.

A component concentration measurement method by the component concentration meter 100 according the present embodiment above will be described with reference to FIG. 6.

Figure 5:
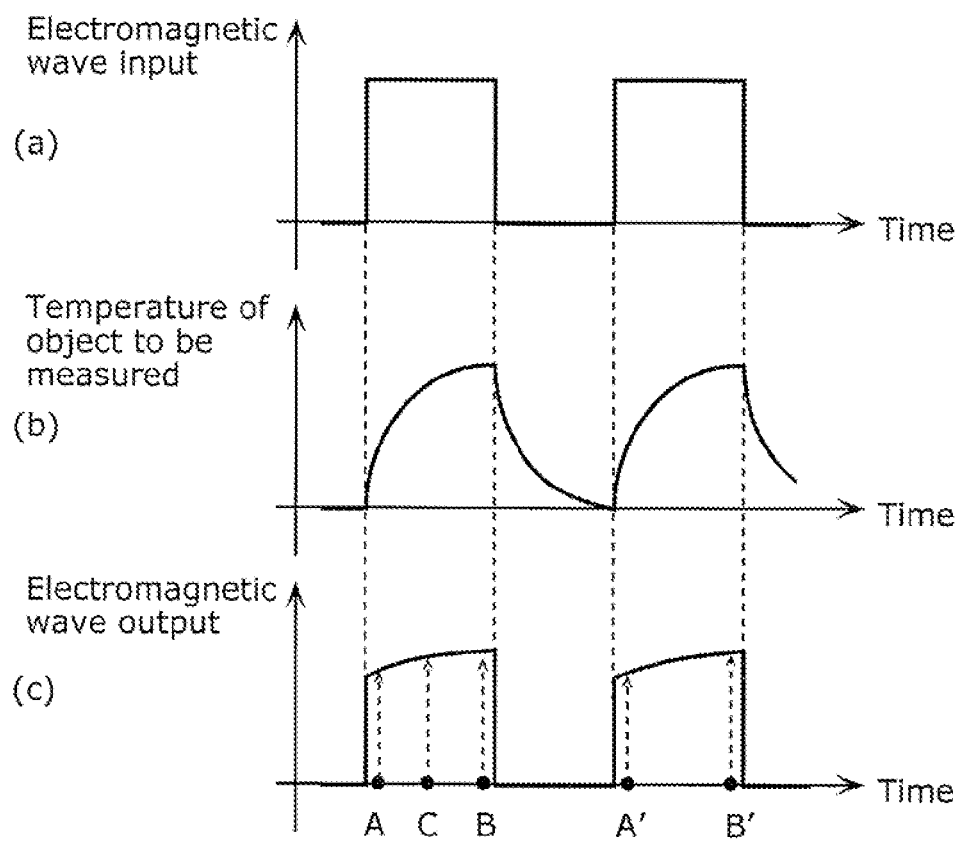
FIG. 5 is (a) a drawing showing an example of a waveform of an electromagnetic wave input to an object to be measured, (b) a drawing showing an example of change in the temperature of the object to be measured, and (c) a drawing showing an example of a waveform of an electromagnetic wave output from the object to be measured.
Figure 6:
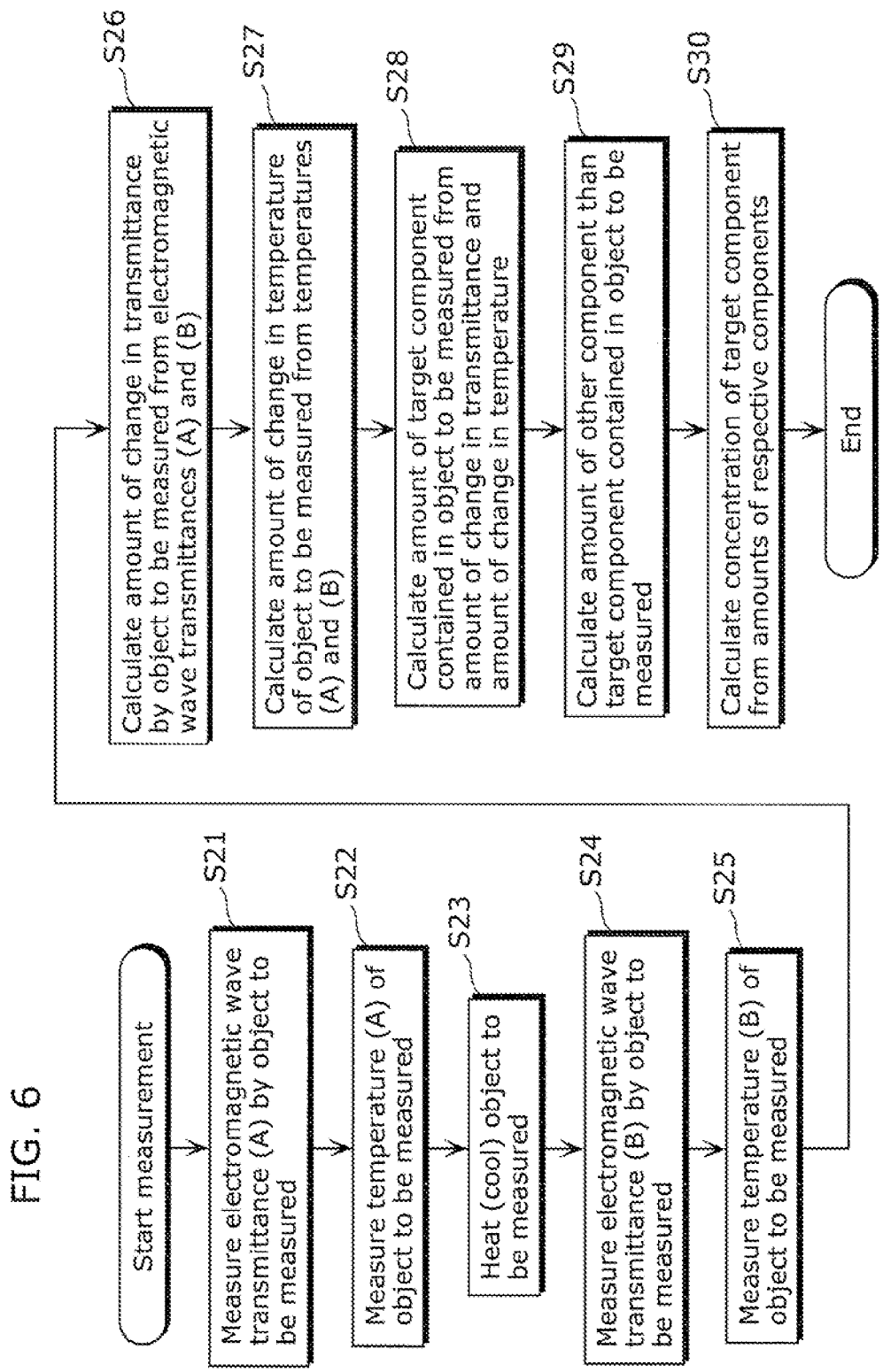
FIG. 6 is a flowchart showing a procedure of measuring a concentration of a component according to Embodiment 1 of the present invention.

As shown in FIG. 6, the component concentration meter 100 according to the present embodiment measures the electromagnetic wave transmittance (A) of the object to be measured 102 and the temperature (A) of the object to be measured 102 under the first condition during irradiation with the electromagnetic wave (for example, at the point A in FIG. 5(c)) (S21 and S22). Next, the component concentration meter 100 continuously irradiates the object to be measured 102 with the electromagnetic wave to heat the object to be measured 102, or stops irradiation with the electromagnetic wave to cool the object to be measured 102 (S23). Next, the component concentration meter 100 measures the electromagnetic wave transmittance (B) of the object to be measured 102 and the temperature (B) of the object to be measured 102 under the second condition during irradiation with the electromagnetic wave (for example, at the point B in FIG. 5(c)) (S24 and S25). Thus, the component concentration meter 100 measures the electromagnetic wave transmittance and temperature of the object to be measured 102 before and after heating (cooling) of the object to be measured 102.

Next, the component concentration meter 100 subtracts one from the other of the measured electromagnetic wave transmittance (A) and the electromagnetic wave transmittance (B) to calculate the amount of change in the transmittance of the object to be measured 102 (S26). Similarly, the component concentration meter 100 subtracts one from the other of the temperature A and the temperature B to calculate the amount of change in the temperature of the object to be measured 102 (S27). Here, the method for calculating the amount of change is not limited to that above. For example, the ratio of the two measured values may be used.

Next, the component concentration meter 100 determines the amount of the target component from the relationship between the amount of change in the electromagnetic wave transmittance and the amount of change in the temperature (S28). The component concentration meter 100 holds the relationship among the difference in the transmittance, the difference in the temperature, and the amount (mass) of the target component in advance.

Next, the component concentration meter 100 measures the amount of other components than the target component contained in the object to be measured 102 (S29). The measurement method is not particularly limited. The conventional method may be used, or the method for measuring the amount of the target component (S21 to S28) may be used. Then, the component concentration meter 100 divides the amount of the target component by the amount of the whole components (amount of the target component+the amount of the other component than the target component) to calculate the concentration of the target component contained in the object to be measured 102 (S30).

In the component concentration meter 100 according to the present embodiment, the temperature of the object to be measured 102 is changed, and the concentration of the target component is calculated from the amount of the light absorptivity to be changed accompanied by the change in the temperature. Thereby, the concentration of the target component can be measured with high accuracy than in the conventional method. Moreover, a configuration without a spectroscopic device can be provided, leading to a more compact and inexpensive component concentration meter.

Further, while the electromagnetic waves having different wavelengths have many causes of measurement errors such as different degrees of scattering, a simple configuration such that the transmittance of the electromagnetic wave in the same optical path is measured at the same wavelength several times can reduce the measurement errors.

Moreover, Embodiment 1 is different from a component concentration meter 300 using a pump-probe method or the like, which will be shown in Embodiment 2. In Embodiment 1, a plurality of electromagnetic wave propagation paths do not need to be overlaid in the object to be measured, and a simpler optical system can be provided. Thereby, an more inexpensive component concentration meter can be provided.

More desirably, as shown in FIG. 4, the component concentration meter includes a filter 106 that transmits only a wavelength at which the absorptivity of the target component changes according to the change in the temperature of the object to be measured 102 in the electromagnetic wave propagation path between the object to be measured 102 and the detecting unit 104. Thereby, the amount of glucose can be measured with higher accuracy.

In the present embodiment, an example using the near-infrared light having a wavelength of not less than 1600 nm and not more than 1900 nm has been shown, but the present invention will not be limited to the configuration using the near-infrared light in the wavelength band. The same effect can be obtained in the measurement of the concentration of glucose even if one of the near-infrared light having a wavelength in the range of not less than 900 nm and not more than 1050 nm and that at a wavelength in the range of not less than 1200 nm and not more than 1270 is used, for example. More desirably, using the filter 106, only the near-infrared light having a wavelength in this range is extracted and detected. Thereby, the amount of glucose can be measured with much higher accuracy.

In the case of the object to be measured 102 having depressions and projections like a human body (a finger), as shown in FIG. 4, the depression projection smoothing material 107 that has substantially the same refractive index as that of the object to be measured 102 and smoothes the depressions and projections of the object to be measured 102 is used. This can suppress change in distribution of the intensity of the electromagnetic wave from the oscillating unit 103 to the detecting unit 104 by the depressions and projections of the object to be measured 102. Thereby, a more compact detecting unit 104 can be used.

As the depression projection smoothing material 107, for example, water or normal saline is used to demonstrate the effect above. Namely, with the finger being put into a water tank containing water, the finger in the water tank is irradiated with the electromagnetic wave, thereby enabling more accurate measurement.

In the case where the electromagnetic wave in the near-infrared range, the visible light range, or ultraviolet range is detected, a photodiode can be used for the detecting unit 104. The photodiode is an inexpensive detecting unit. Time resolution is increased as the surface to be detected is smaller. Accordingly, scattering of the electromagnetic wave is suppressed if the depression projection smoothing material 107 is used, thereby to improve the accuracy of the measurement.

Desirably, as the detecting unit 104, other than the photodiode, a photo multiplier tube having high time resolution is used. Thereby, the amount of the transmittance to be changed can be measured more accurately, and the amount of glucose can be measured with higher accuracy.

Desirably, as shown in FIG. 4, a converging lens (electromagnetic wave converging unit) 108 configured to converge the electromagnetic wave 101 oscillated from the oscillating unit 103 is provided in the electromagnetic wave propagation path between the oscillating unit 103 and the object to be measured 102. Thereby, uniformity of the intensity of the electromagnetic wave in the propagation direction is enhanced.

Figure 7:
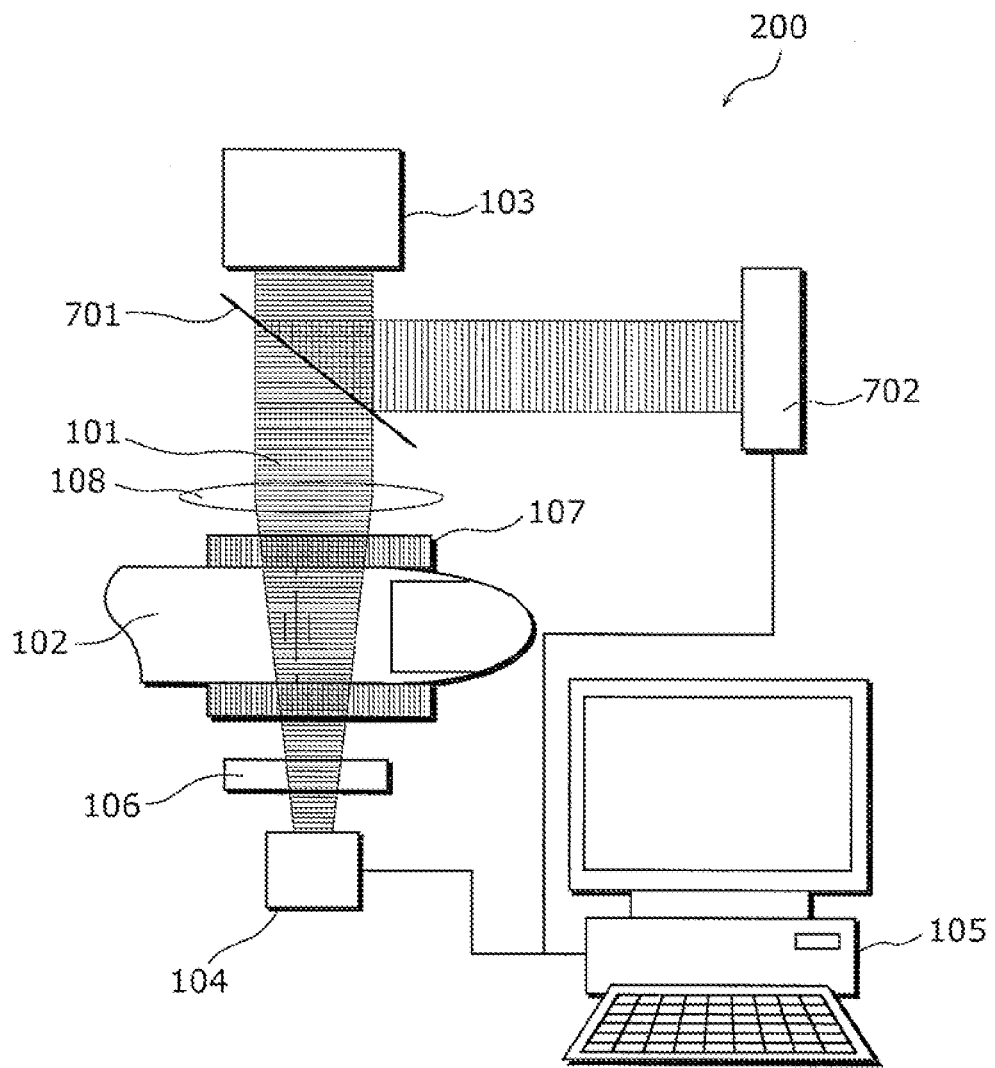
FIG. 7 is a drawing of a schematic configuration of a modification of the component concentration meter according to Embodiment 1 of the present invention.

As a modification of FIG. 4, desirably, as a component concentration meter 200 shown in FIG. 7, part of the electromagnetic wave 101 emitted from the oscillating unit 103 is reflected by a separating mirror 701 to detect the output by the detecting unit 702. The output from the oscillating unit is monitored by the detecting unit 702 to compare the output with an output value detected by the detecting unit 104. Thereby, the change of the transmittance in the object to be measured 102 can be measured more accurately. Thereby, the accuracy of the measurement of the concentration of the component is further improved.

In the present embodiment, the driving pulse waveform of the oscillating unit 103 is rectangular. The driving pulse waveform of the oscillating unit 103, however, may not always be rectangular. At least, as long as the temperature of the object to be measured 102 is changed according to the electromagnetic wave to be input to the object to be measured 102, the amount of glucose can, be determined from the change in the transmittance and that in the temperature.

Embodiment 2

Figure 8:
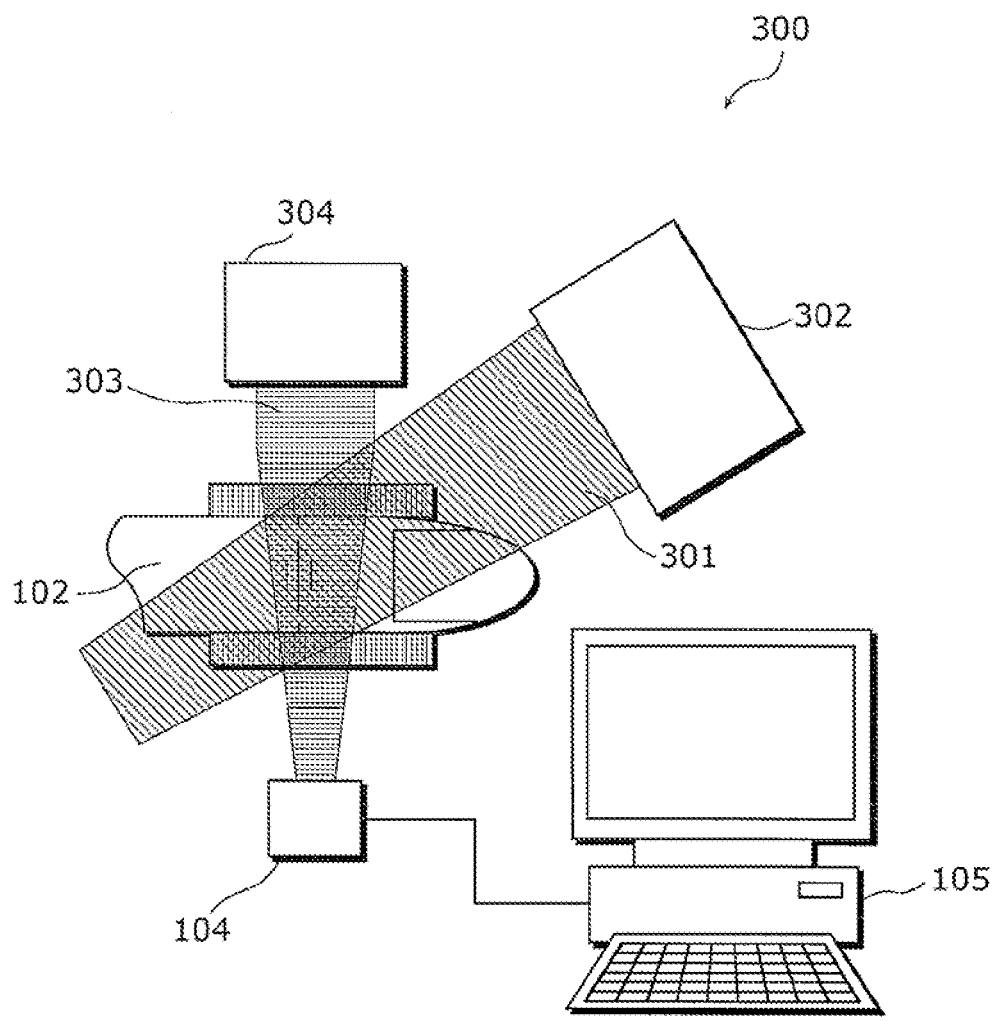
FIG. 8 is a drawing of a schematic configuration of a component concentration meter according to Embodiment 2 of the present invention.

FIG. 8 is a drawing showing a schematic configuration of a component concentration meter 300 according to Embodiment 2 of the present invention.

Here, similarly to Embodiment 1, the component concentration meter 300 that measures the concentration of glucose contained in the blood vessel of a finger as an example of the object to be measured 102 will be described. Detailed description of the same parts as those in Embodiment 1 will be omitted, and the differences will be mainly described. Same reference numerals are given to the same components as those in Embodiment 1.

As shown in FIG. 8, the component concentration meter 300 according to the present embodiment includes oscillating units 302 and 304, a detecting unit 104, and a computing unit 105. The component concentration meter 300 may further include a filter 106 and a converging lens 108, which are not illustrated.

The oscillating unit 302 oscillates an electromagnetic wave for heating 301 that heats the object to be measured 102. On the other hand, the oscillating unit 304 oscillates an electromagnetic wave for detection 303 that transmits the object to be measured 102 to be detected by the detecting unit 104. The oscillating units 302 and 304 are arranged such that the propagation path of the electromagnetic wave for heating 301 may be overlaid on that of the electromagnetic wave for detection 303 within the object to be measured 102.

In this case, desirably, the property of the electromagnetic wave for detection 303 to be changed according to the change in the temperature of the object to be measured 102 is changed more largely than that of the electromagnetic wave for heating 301. On the other hand, desirably, the electromagnetic wave for heating 301 has an absorptivity by the object to be measured 102 larger than that of the electromagnetic wave for detection 303.

Specifically, in the present Embodiment 2, as the electromagnetic wave for detection 303, the near-infrared light having a wavelength of not less than 1600 nm and not more than 1900 nm (first wavelength) can be used, for example. As the electromagnetic wave for heating 301, the mid-infrared light having a wavelength of not less than 2 μm (second wavelength) is used, for example. Use of the electromagnetic wave in the mid-infrared range having higher absorptivity by glucose can increase the temperature more largely, leading to more accurate measurement of the concentration of the component.

Moreover, the oscillating units 302 and 304 are driven such that the electromagnetic wave for heating and the electromagnetic wave for detection both may have the waveform shown in FIG. 5(*a*), and the concentration of the component is measured according to the flowchart shown in FIG. 6. Thereby, the same effect as that in Embodiment 1 is obtained.

In Embodiment 1, the electromagnetic wave that heats the object to be measured 102 and the electromagnetic wave detected by the detecting unit 104 are oscillated from the same oscillating unit 103. Thereby, the optical system is simplified. For this reason, a more inexpensive component concentration meter 100 can be provided. In the present invention, however, the electromagnetic wave that heats the object to be measured 102 and the electromagnetic wave detected by the detecting unit 104 may not be always oscillated by the same oscillating unit 103.

Desirably, the electromagnetic wave for heating 301 has a high absorptivity by the target component whose concentration is to be measured, and a low absorptivity by other component than the target component contained in the object to be measured 102. Desirably, the electromagnetic wave for heating 301 has a wavelength that can be oscillated by an inexpensive and large-output oscillating unit 302 already commercially available as a product.

Contrary to this, the electromagnetic wave for detection 303 needs to have an absorptivity that largely changes according to the temperature of the target component. The electromagnetic wave for heating 301 and the electromagnetic wave for detection 303 have different requirements from each other. Accordingly, depending on the case, an optimal wavelength of the electromagnetic wave is different for each of the electromagnetic wave for heating 301 and the electromagnetic wave for detection 303. Independent selection of the optimal wavelength further improves the accuracy of the measurement.

In the present embodiment, the amount of glucose may be determined from the difference in the transmittance measured several times using the pump-probe method. The case where the pump-probe method is used for the present embodiment will be described below.

Figure 9:
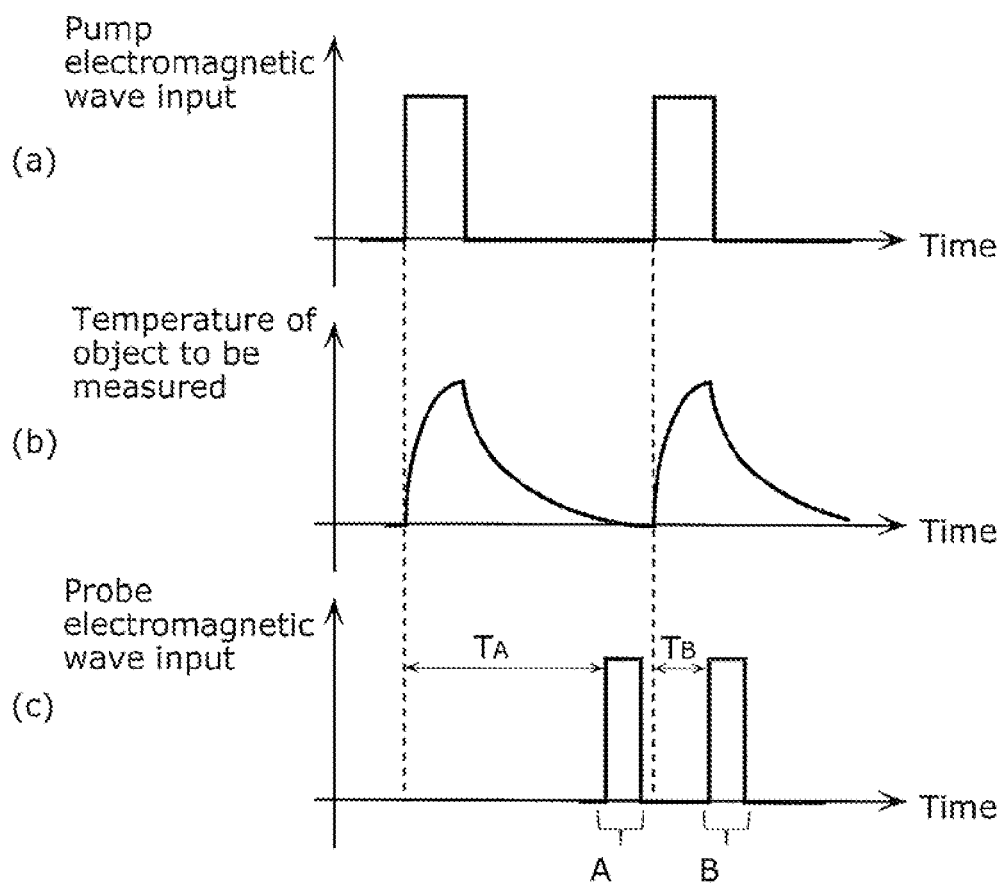
FIG. 9 is (a) a drawing showing an example of a waveform of a pump electromagnetic wave input to an object to be measured, (b) a drawing showing an example of change in the temperature of the object to be measured, and (c) a drawing showing an example of a waveform of a probe electromagnetic wave input to the object to be measured.

First, as shown in FIG. 9(a), by pulse irradiation with a pump electromagnetic wave (electromagnetic wave for heating), the temperature of the object to be measured 102 is gradually increased during the pulse irradiation with the pump electromagnetic wave as shown in FIG. 9(b), and gradually reduced when the irradiation with the pump electromagnetic wave is terminated.

Moreover, the object to be measured 102 is pulse irradiated with a probe electromagnetic wave (electromagnetic wave for detection) while the time difference from the pulse of the pump electromagnetic wave is controlled as shown in FIG. 9(c). The transmittance is detected by the detecting unit 104 at a measurement time A and a measurement time B. An output interval TA between the probe electromagnetic wave pulse and the pump electromagnetic wave pulse and an output interval TB therebetween are set at different values.

More specifically, for a period of time including the measurement time A, pulse irradiation with the probe electromagnetic wave is performed $T_A$ seconds after the pulse irradiation with the pump electromagnetic wave. On the other hand, for a period of time as including the measurement time B, pulse irradiation with the probe electromagnetic wave is performed $T_B$ ($<T_A$) after the pulse irradiation with the pump electromagnetic wave. Thereby, the temperature of the object to be measured 102 at the measurement time A is different from that at the measurement time B, and the transmittances detected by the detecting unit 104 are different. Then, the amount of glucose can be determined from the difference in the transmittance and difference in temperature at the two measurement times A and B.

Use of the pump-probe method for the present embodiment can capture rapid change of the transmittance, improving the accuracy of the measurement.

In the case where the pump-probe method as above is used, rapid change of the transmittance can be measured. Thereby, change of the transmittance caused by more phenomena can be measured.

For example, saturated absorption can be caused by the pump electromagnetic wave to measure the transmittance with the probe electromagnetic wave. In each period of time for measurement, the transmittance of the probe electromagnetic wave is measured at an irradiation timing with the pump electromagnetic wave and at that with the probe electromagnetic wave different from the irradiation timing with the pump electromagnetic wave. Thereby, the recovery rate of the absorptivity is determined from the difference in the transmittance. Namely, the absorptivity of a substance is temporarily reduced by saturated absorption, and then, recovered. Each substance has its own recovery rate of the absorptivity after saturated absorption. For this reason, the substances are distinguished for each recovery rate, and the amount of each substance can be determined by the amount of recovery. Then, in the present embodiment, the object to be measured may be irradiated with the electromagnetic waves at a plurality of wavelengths, and the amount of the other component than the target component contained in the object to be measured may be determined from the transmittance of each wavelength by the multivariate analysis.

Desirably, however, similarly to the case of glucose, the amount of the other component than glucose contained in the object to be measured is determined from the difference in the recovery rate of the absorptivity after saturated absorption or the amount of the transmittance to be changed at a specific wavelength at which the absorptivity changes depending on the change in the temperature. Thereby, the amount of the other component than glucose can be measured with higher accuracy, leading to more accurate calculation of the concentration of glucose.

Thus, if the method for measuring a concentration of a target component based on the recovery rate from saturated absorption is used, accuracy of the measurement of the concentration can be enhanced also in a component having no wavelength at which the transmittance of electromagnetic wave changes according to the temperature.

On the other hand, in the method for measuring a concentration of a target component based on the change in the transmittance of the electromagnetic wave according to the change in the temperature, no electromagnetic wave oscillating unit having a high peak power that produces saturated absorption is needed, and the concentration of the component can be measured at low cost with high accuracy.

More desirable is the measurement of the concentration of the component using both of the properties unique to a substance, i.e., the change in the transmittance of the electromagnetic wave according to the change in the temperature and the recovery rate from saturated absorption. This can provide a component concentration meter with higher accuracy in a wider variety of substances than in the measurement of the concentration of the component using only one of the properties thereof.

In the pump-probe method, a method may be used in which the electromagnetic wave produced by one oscillating unit is once branched, and the propagation paths of the branched electromagnetic waves are adjusted such that the branched electromagnetic waves may be overlaid within the object to be measured. In this case, a mechanism that adjusts an optical distance between the two branched propagation paths can be provided to adjust the time difference between the pump electromagnetic wave and the probe electromagnetic wave. In the method, without synchronizing the two light sources with each other, the time difference between the pump electromagnetic wave and the probe electromagnetic wave can be adjusted with high accuracy. Thereby, the accuracy of the measurement can be improved with an inexpensive configuration.

In the case where the electromagnetic wave produced by one oscillating unit is once branched, and the branched electromagnetic waves are overlaid within the object to be measured, the wavelength of one of the electromagnetic waves may be converted from the time when the electromagnetic wave is branched and until the branched the electromagnetic waves enter the object to be measured. Thereby, accurate measurement of the concentration of the component can be provided with respect to more substances. Conversion of the wavelength is desirably performed using a nonlinear optical crystal, and may be performed using a nonlinear optical crystal having a periodically domain-inverted structure formed therein. This enables highly efficient conversion of the wavelength, leading to reduction in the power consumed by the oscillating unit. This also enables reduction in the size of the apparatus.

Desirably, the electromagnetic wave produced by one oscillating unit is passed through a wavelength converting device such as a nonlinear optical crystal to convert part of the wavelength, and is separated into two of the electromagnetic wave produced by conversion of the wavelength and the electromagnetic wave having the original wavelength, which is passed through the wavelength converting device without converting the wavelength. This enables more reduction in the power consumed by the oscillating unit, and reduction in the size of the apparatus.

Embodiment 3

Figure 10:
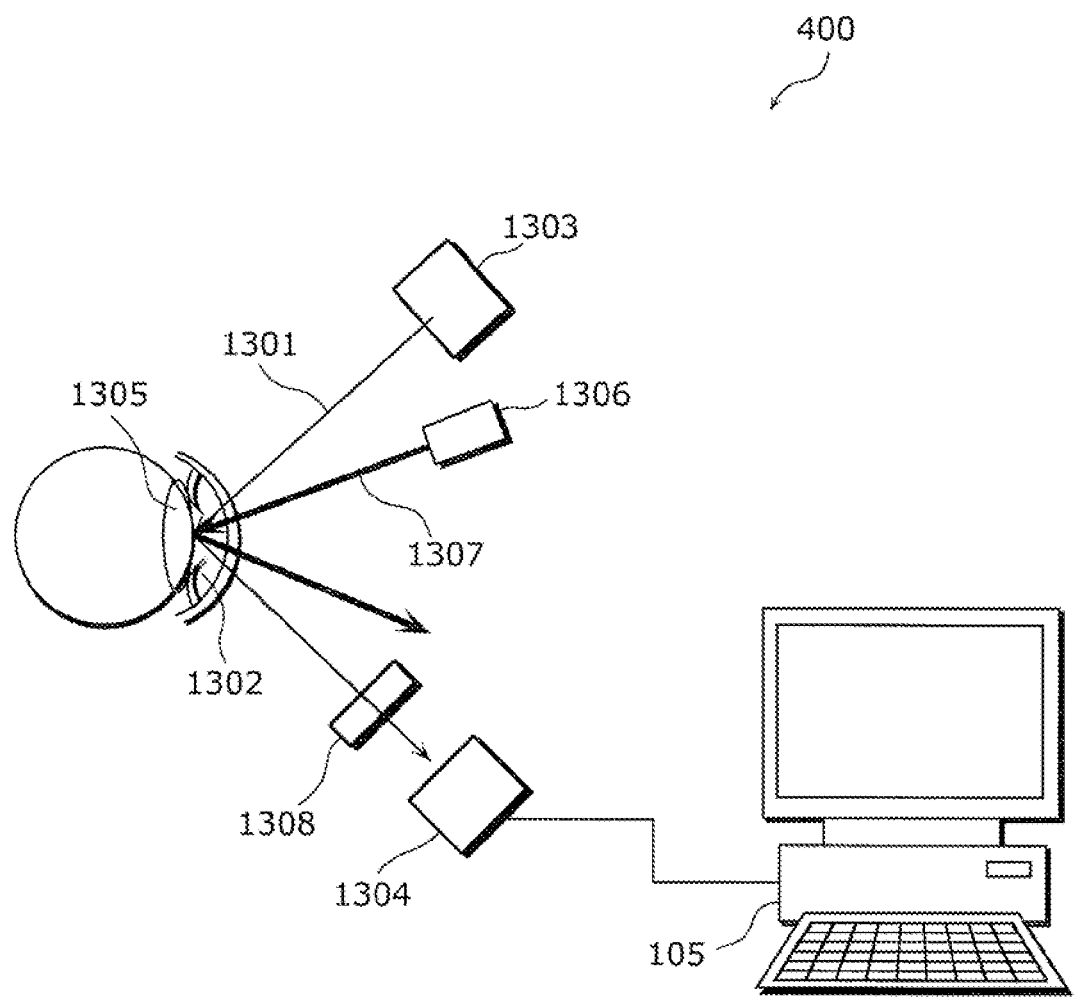
FIG. 10 is a drawing showing a schematic configuration of a component concentration meter according to Embodiment 3 of the present invention.

FIG. 10 is a drawing showing a schematic configuration of a component concentration meter 400 according to Embodiment 3 of the present invention. In the present embodiment, the component concentration meter 400 that measures the concentration of glucose contained in an anterior aqueous humor in an eye 1302 as an example of the object to be measured will be described. Detailed description of the same parts as those in Embodiments 1 and 2 will be omitted, and the differences will be mainly described. Same reference numerals are given to the same components as those in Embodiments 1 and 2.

As shown in FIG. 10, the component concentration meter 400 according to the present embodiment includes oscillating units 1303 and 1306, a detecting unit 1304, a rotary polarized wave separator (rotary polarized wave separating unit) 1308, and a computing unit 105. The oscillating unit 1306 can be eliminated as described later.

The component concentration meter 400 irradiates an anterior segment of an eyeball with an electromagnetic wave 1301 oscillated by the oscillating unit 1303. The tissue of the crystalline lens 1305 has a refractive index different from that of the anterior aqueous humor in an eye 1302. The reflected electromagnetic wave 1301 is guided to the detecting unit 1304. In the present embodiment, similarly to Embodiments 1 and 2, the near-infrared light having a wavelength in the range of not less than 1600 nm not more than 1900 nm can also be used as the electromagnetic wave 1301, for example.

In the present embodiment, while the object to be measured is as different from those in Embodiments 1 and 2, the same effect can be obtained by the same method. For example, the oscillating unit 1303 is driven so as to provide a waveform as shown in FIG. 5(a), and the concentration of the component is measured according to the flowchart in FIG. 6 to provide the same effect as that in Embodiment 1. Here, the electromagnetic wave 1301 can be used as both of the electromagnetic wave for heating and the electromagnetic wave for detection in the same manner as in Embodiment 1, and the oscillating unit 1306 can be eliminated.

Similarly to Embodiment 2, the electromagnetic wave 1301 oscillated from the oscillating unit 1303 is used as the electromagnetic wave for detection, an electromagnetic wave 1307 oscillated from the oscillating unit 1306 is used as the electromagnetic wave for heating, and the two electromagnetic waves can be overlaid within the anterior aqueous humor in an eye 1302. With such a configuration, the oscillating units 1303 and 1306 are driven such that the electromagnetic wave for heating and the electromagnetic wave for detection both may have the waveform shown in FIG. 5(a), and the concentration of the component is measured according to the flowchart shown in FIG. 6. Thus, the same effect as that in Embodiment 2 can be obtained.

In the present embodiment, the amount of glucose can also be determined from the difference in the transmittance and difference in temperature measured several times using the pump-probe method in the same manner as in Embodiment 2. More desirable is measurement of the concentration of the component using both of the change in the transmittance of the electromagnetic wave according to the change in the temperature and the recovery rate from saturated absorption. Thereby, a component concentration meter with higher accuracy can be provided.

The anterior aqueous humor in an eye 1302 contains approximately 61% sugar of the blood concentration thereof, and has relatively good followability to the blood concentration. Accordingly, the blood concentration of glucose can be expected using the component concentration meter 400 shown in the present embodiment.

The anterior aqueous humor in an eye 1302 contains little substance that obstructs the measurement of the concentration of sugar (causes scattering of the electromagnetic wave or the like). Accordingly, the configuration of the present embodiment is desirably used. This enables the measurement of the concentration with higher accuracy. For example, in the case where change in the transmittance of the near-infrared light having a wavelength in the range of not less than 900 nm and not more than 1050 nm is measured, reduction in the accuracy of the measurement caused by absorption by hemoglobin and melanin in the blood can be suppressed.

Use of the anterior aqueous humor in an eye 1302 as the object to be measured enables the measurement of the concentration of the component using an electromagnetic wave in the range of the visible light and the ultraviolet light. Thereby, a more compact component concentration meter 400 can be provided.

Glucose has photoactivity, and therefore has optical rotation. The optical rotation refers to a phenomenon that when a left circularly polarized wave and a right circularly polarized wave propagate within a photoactive substance such as glucose, the polarization state at the time of emission is different from that at the time of entering because the left circularly polarized wave has a refractive index different from that of the right circularly polarized wave. Thereby, the polarized plane of the linearly polarized wave that is the sum of the left circularly polarized wave and the right circularly polarized wave rotates according to the optical rotation and concentration of the substance. Accordingly, the concentration of the substance can be determined by measurement of the amount of the polarized plane to be rotated if the optical rotation of the substance is known.

Even in the substance having photoactivity, in the case where the electromagnetic wave reciprocates in the same propagation path (in the case where a distance of propagation within the object to be measured before reflection is equal to that after reflection), rotation of the polarized plane by optical rotation is eliminated. Then, in the present embodiment, as shown in FIG. 10, the electromagnetic wave desirably enters inclined to the front surface of the crystalline lens 1305 to be reflected. Namely, desirably, the optical path is set such that the distance of propagation within the object to be measured before reflection may be different from that after reflection. Thereby, rotation of the polarized plane by optical rotation is not eliminated, leading to the measurement of the concentration of the component with high accuracy.

In the present embodiment, desirably, the electromagnetic wave 1301 is a linearly polarized wave, and the component concentration meter includes a rotary polarized wave separator 1308 between the anterior aqueous humor in an eye 1302 and the detecting unit 1304. This enables the measurement of the concentration of the component using the two parameters, i.e., the amount of the transmittance to be changed accompanied by the change in the temperature and the amount of the optical rotation to be changed. As a result, the concentration of the component can be measured with higher accuracy with respect to more components. More desirably, the amount of the rotation angle to be changed in the polarization direction accompanied by the change in the temperature is measured. The optical rotation is calculated from these, and used for determination of the concentration of the target component. This enables the measurement of the concentration of the component with higher accuracy.

Here, as the rotary polarized wave separator 1308, a branch-line polarized wave separator can be used, for example. In the case where the electromagnetic wave has a wavelength from the near-infrared light to the ultraviolet light, a Glan Taylor polarizer and a Glan Thompson polarizer can be used.

Embodiment 4

Figure 11:
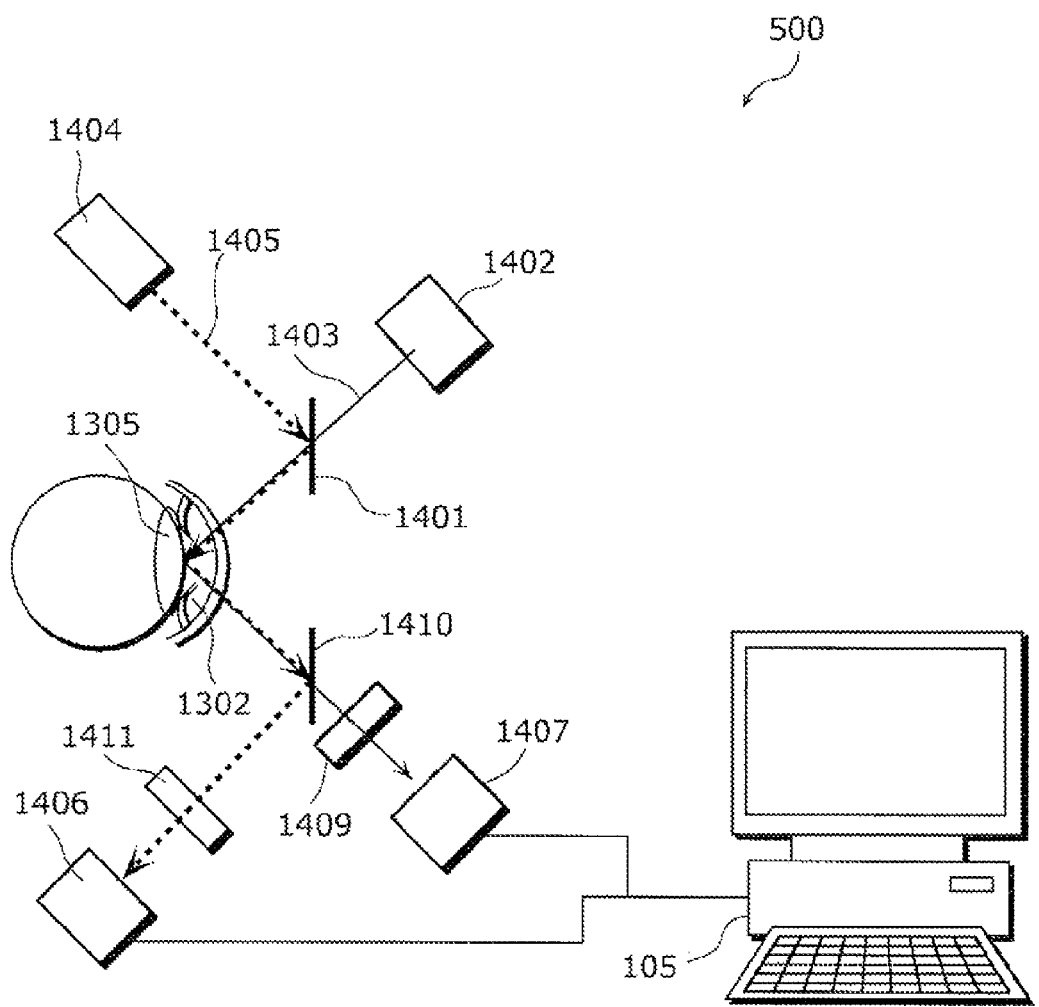
FIG. 11 is a drawing showing a schematic configuration of a component concentration meter according to Embodiment 4 of the present invention.

FIG. 11 is a drawing showing a schematic configuration of a component concentration meter 500 according to Embodiment 4 of the present invention. In the present embodiment, the component concentration meter 500 that measures the concentration of glucose contained in the anterior aqueous humor in an eye 1302 as an example of the object to be measured will be described. Detailed description of the same parts as those in Embodiments 1 to 3 will be omitted, and the differences will be mainly described. Same reference numerals are given to the same components as those in Embodiments 1 to 3.

As shown in FIG. 11, the component concentration meter 500 according to the present embodiment includes oscillating units 1402 and 1404, detecting units 1406 and 1407, dichroic mirrors 1401 and 1410, rotary polarized wave separators 1409 and 1411, and a computing unit 105. The component concentration meter 500 overlays electromagnetic waves 1403 and 1405 respectively oscillated from the oscillating units 1402 and 1402 within the anterior aqueous humor in an eye 1302.

The electromagnetic waves 1403 and 1405 are the linearly polarized wave, and the electromagnetic wave 1403 has a wavelength different from that of the electromagnetic wave 1405. The electromagnetic wave 1405 is reflected, and the dichroic mirror 1401 that transmits the electromagnetic wave 1403 is arranged between the oscillating units 1404 and 1402 and the anterior aqueous humor in an eye 1302 such that the propagation paths of the electromagnetic waves 1403 and 1405 within the anterior aqueous humor in an eye 1302 may coincide with each other. Namely, the dichroic mirror 1401 functions as a synthesizing unit configured to synthesize the electromagnetic waves 1403 and 1405 each having a different wavelength and outputs the synthesized electromagnetic wave to the anterior aqueous humor in an eye 1302 as the object to be measured.

Further, the electromagnetic waves 1403 and 1405 reflected by the crystalline lens 1305 and emitted from the anterior aqueous humor in an eye 1302 are separated by the dichroic mirror 1410 (that transmits the electromagnetic wave 1403, and reflects the electromagnetic wave 1405). Namely, the dichroic mirror 1410 functions a separating unit configured to separate the electromagnetic wave passed through the anterior aqueous humor in an eye 1302 into the electromagnetic waves 1403 and 1405 each having a different wavelength.

Then, the separated electromagnetic waves 1403 and 1405 enter the rotary polarized wave separators 1409 and 1411, respectively. The polarization components passed through the rotary polarized wave separators 1409 and 1411 are acquired by the detecting units 1407 and 1406, respectively.

As shown here, a plurality of electromagnetic waves that are the linearly polarized wave and each have a different wavelength enters the object to be measured, and both the change in the polarization direction and the change in ellipticity within the object to be measured can be determined. This can improve the accuracy of the measurement of the concentration of the component according to the difference in the property, i.e., optical rotation and circular dichroism.

Here, the circular dichroism refers to a phenomenon that the absorption coefficient of the right circularly polarized wave within a substance is different from that of the left circularly polarized wave within a substance. For this phenomenon, the entered linearly polarized wave changes into the elliptically polarized wave. The circular dichroism occurs only in the electromagnetic wave at a wavelength unique to the substance, and the change in the ellipticity depends on the concentration of the substance. For this reason, the circular dichroism can be used for the measurement of the concentration of the component as described above.

In the case of the substance having both of the properties, i.e., the optical rotation and the circular dichroism, however, it is difficult to distinguish the optical rotation from the circular dichroism. For this reason, desirably, a plurality of electromagnetic waves each having a different wavelength enter the object to be measured in the same propagation path, and the rotation angle in the polarization direction and the ellipticity are determined for each wavelength.

Namely, desirably, the propagation paths within the object to be measured of the plurality of electromagnetic waves each having a different wavelength are made to coincide with each other using a device (dichroic mirror 1401) that makes the propagation paths within the object to be measured (anterior aqueous humor in an eye 1302) of the electromagnetic waves at a plurality of wavelengths (electromagnetic waves 1403 and 1405 in the example of FIG. 11). Thereby, the optical rotation is distinguished from the circular dichroism, leading to increased accuracy of the measurement of the concentration of the component.

In the present invention; the change in the polarization direction by scattering within the object to be measured, in the polarization direction by the optical rotation and circular dichroism, and the change in the ellipticity can be distinguished. For this reason, in the case where the object to be measured containing more scattering bodies such as a finger, an earlobe, and an arm is used as in the examples shown in Embodiments 1 and 2, optical rotation, the accuracy can also be significantly enhanced in the measurement of the concentration of the component according to the difference in the optical rotation and that in the circular dichroism.

Namely, in the object to be measured containing a scattering body, the concentration of glucose can be measured according to the difference in the optical rotation and that in the circular dichroism more accurately than the methods in Embodiments 1 and 2. This measurement method can measure the concentration of glucose with less delay of time than in Embodiment 3. In the same manner, the accuracy of the measurement can be improved in all the component concentration meters that estimate the concentration of the target component from the change in the polarization direction within the object to be measured, using the object to be measured containing a scattering body.

Desirably, of the plurality of electromagnetic waves each having a different wavelength, at least one electromagnetic wave is in a wavelength band having substantially no (extremely small) influence of the target component on the circular dichroism, and is used only for determination of the optical rotation of the target component. The amount of rotation by optical rotation in the polarization direction is inversely proportional to the wavelength of the electromagnetic wave. Accordingly, the change by optical rotation in the polarization direction in an electromagnetic wave at any wavelength can be determined. Thereby, the two phenomena, i.e., the optical rotation and the circular dichroism can be distinguished with higher accuracy. Namely, the accuracy of the measurement of the concentration of the component can be improved.

Similarly to Embodiment 1, the oscillating units are driven such that the electromagnetic wave to be input to the object to be measured may have the waveform shown in FIG. 5(a), and the concentration of the component is measured according to the flowchart shown in FIG. 6. Thereby, the concentration of the component can be measured according to the change in the property, i.e., the optical rotation and circular dichroism according to the change in the temperature, enabling more accurate measurement of the concentration of the component.

Further, the electromagnetic wave 1405 oscillated from the oscillating unit 1404 may be used as the electromagnetic wave for detection, and the electromagnetic wave 1403 oscillated from the oscillating unit 1402 may be used for the electromagnetic wave for heating. In this case, the rotary polarized wave separator 1409 and the detecting unit 1407 can be eliminated. The electromagnetic wave 1405 may be used as the electromagnetic wave for heating, and the electromagnetic wave 1403 may be used as the electromagnetic wave for detection.

Embodiment 5

Figure 12:
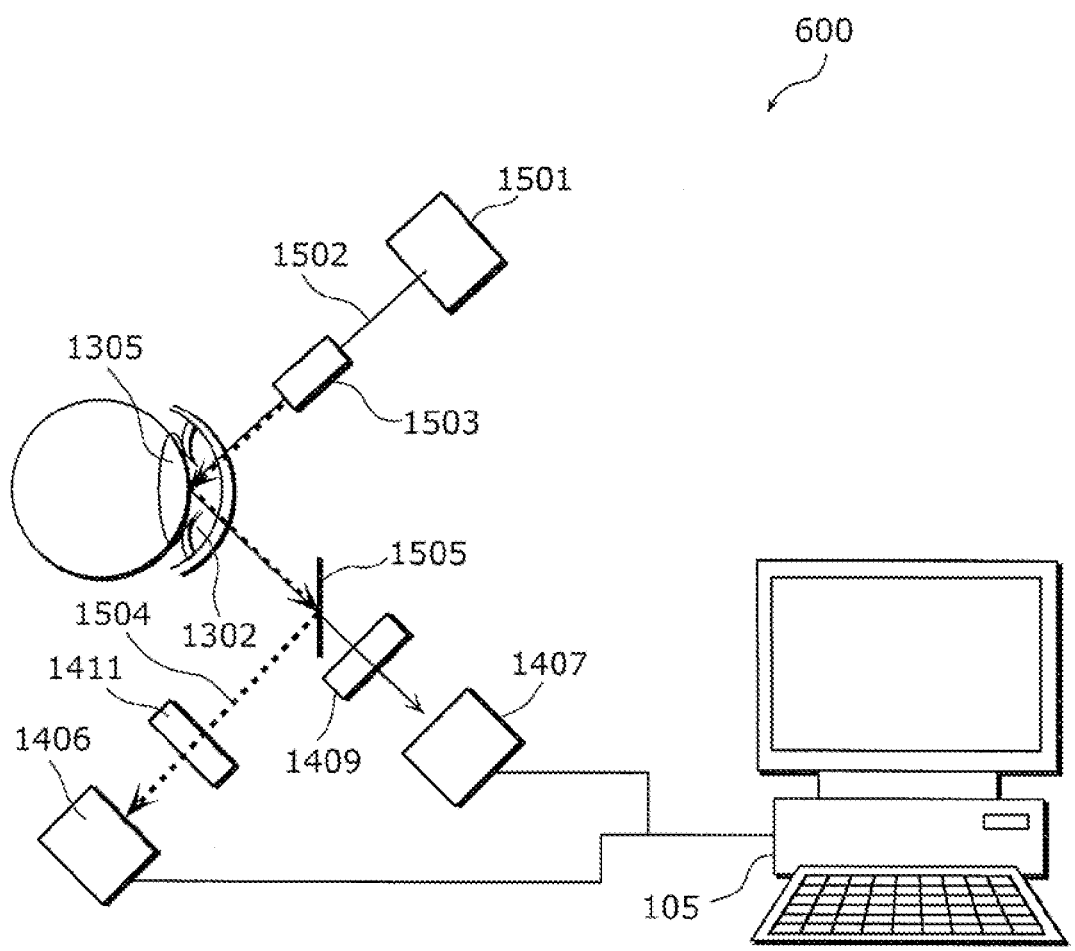
FIG. 12 is a drawing showing a schematic configuration of a component concentration meter according to Embodiment 5 of the present invention.

FIG. 12 is a drawing showing a schematic configuration of a component concentration meter 600 according to Embodiment 5 of the present invention. In the present embodiment, the component concentration meter 600 that measures the concentration of glucose contained in the anterior aqueous humor in an eye 1302 as an example of the object to be measured will be described. Detailed description of the same parts as those in Embodiments 1 to 4 will be omitted, and the differences will be mainly described. Same reference numerals are given to the same components as those in Embodiments 1 to 4.

As shown in FIG. 12, the component concentration meter 600 according to the present embodiment includes an oscillating unit 1501 that produces a first electromagnetic wave 1502, a wavelength converting unit 1503 configured to convert part of the first electromagnetic wave 1502 into a second electromagnetic wave 1504 having a different wavelength, rotary polarized wave separators 1409 and 1411, detecting units 1406 and 1407, and a computing unit 105.

The second electromagnetic wave 1504 and the first electromagnetic wave 1502 passed through the wavelength converting unit 1503 without being converted into the second electromagnetic wave 1504 both enter the anterior aqueous humor in an eye 1302 as the object to be measured, reflected by the crystalline lens 1305, and emitted from the anterior aqueous humor in an eye 1302 to be separated by the dichroic mirror 1505 (that transmits the electromagnetic wave 1502, and reflects the electromagnetic wave 1504).

Then, the first electromagnetic wave 1502 enters the rotary polarized wave separator 1409. The power of the polarization component passed through the rotary polarized wave separator 1409 is detected by the detecting unit 1407. Similarly, the second electromagnetic wave 1504 enters the rotary polarized wave separator 1411. The power of the polarization component passed through rotary polarized wave separator 1411 is detected by the detecting unit 1406.

In the present embodiment, similarly to Embodiment 4, a plurality of electromagnetic waves that is the linearly polarized wave and each has a different wavelength enters the object to be measured, and both the change in the polarization direction and the change in ellipticity within the object to be measured can be determined. This can improve the accuracy of the measurement of the concentration of the component according to the difference in the property, i.e., optical rotation and circular dichroism.

In the present embodiment, the plurality of electromagnetic waves that is the linearly polarized wave and each has a different wavelength is produced by the wavelength converting unit 1503. Thereby, the phase difference between the respective electromagnetic waves (electromagnetic wave 1502 and electromagnetic wave 1504 in the example of FIG. 12) can be constant, and the propagation paths can be made to completely coincide with each other. Thereby, the rotation by the optical rotation and circular dichroism in the polarization direction can be distinguished from the change by scattering in the polarization direction more accurately than in Embodiment 4, improving the accuracy of the measurement.

Additionally, a device for making the propagation paths of the plurality of electromagnetic waves coincide with each other is unnecessary. The optical system can be simplified and the number of adjustment steps can be reduced, therefore leading to reduction in cost and size of the apparatus.

Desirably, the wavelength converting unit 1503 converts the electromagnetic wave 1502 into an electromagnetic wave that is a harmonic of the electromagnetic wave 1502 (frequency is an integer multiple of that of the electromagnetic wave 1502). The phase difference between the plurality of electromagnetic waves is fixed. If the wavelength is an integer multiple, the peak value of amplitude of an electric field in the synthesized electromagnetic wave can be stabilized. Thereby, the synthesized wave of the plurality of electromagnetic waves prevents nonlinear absorption such as two-photon absorption from causing measurement errors within the object to be measured, leading to more accurate measurement of the concentration of the component.

This effect is desirable because the same effect is demonstrated not only in the component concentration meter based on the difference in the property, i.e., the optical rotation and circular dichroism, but also in the component concentration meter based on the difference in the absorptivity of the light. Desirably, also in the configurations in Embodiments 2 to 4, of the electromagnetic waves to enter the object to be measured, at least one electromagnetic wave is an electromagnetic wave produced from at least other one electromagnetic wave by a wavelength conversion technique.

Similarly to Embodiment 1, desirably, the oscillating unit is driven such that the electromagnetic wave input may have the waveform shown in FIG. 5(a), and the concentration of the component is measured according to the flowchart shown in FIG. 6. Thereby, the concentration of the component can be measured from the change in the property, i.e., the optical rotation and circular dichroism according to the change in the temperature, leading to more accurate measurement of the concentration of the component.

Similarly to Embodiment 3, desirably, the component concentration meter according to the present embodiment includes an oscillating unit configured to oscillate the electromagnetic wave for heating to heat the propagation paths of the electromagnetic waves 1502 and 1504 within the object to be measured. Thereby, the amount of glucose can be determined from the difference in the transmittance measured several times using the pump-probe method. Namely, the measurement of the concentration of the component using both of the change in the transmittance of the electromagnetic wave according to the change in the temperature and the recovery time from saturated absorption can be performed, providing a component concentration meter with higher accuracy.

Further, the first electromagnetic wave 1502 may be used as the electromagnetic wave for detection, and the second electromagnetic wave 1504 may be used as the electromagnetic wave for heating. In this case, the rotary polarized wave separator 1411 and the detecting unit 1406 can be eliminated. The first electromagnetic wave 1502 may be used as the electromagnetic wave for heating, and the second electromagnetic wave 1504 may be used as the electromagnetic wave for detection.

Figure 13:
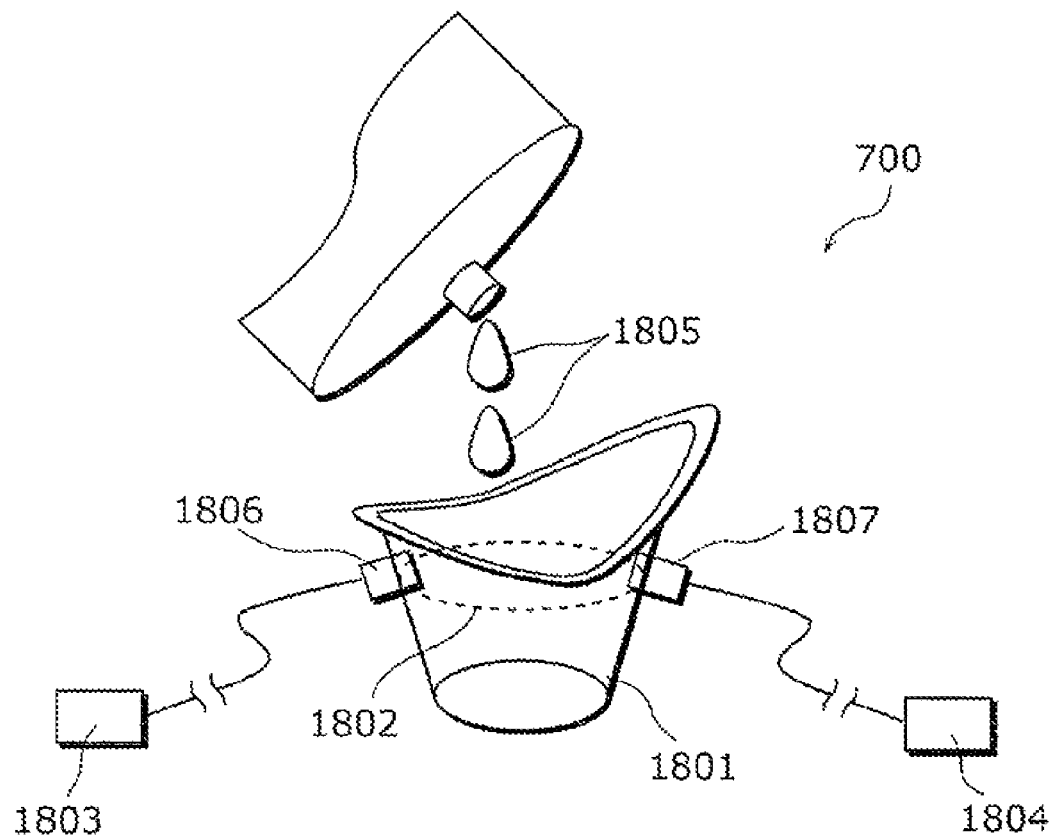
FIG. 13 is a drawing showing a schematic configuration of a cup for irradiation with an electromagnetic wave.

In the case where an eyeball is irradiated with an electromagnetic wave as Embodiments 3 to 5, a component concentration meter 700 including a cup for irradiation with an electromagnetic wave 1801 as shown in FIG. 13 is desirably used.

Hereinafter, the cases where the component concentration meter 700 including the cup for irradiation with an electromagnetic wave 1801 is used in Embodiments 3 to 5 will be collectively described. The electromagnetic waves 1301, 1307, 1403, 1405, 1502, and 1504 in Embodiments 3 to 5 will be collectively described as an electromagnetic wave 1901.

The cup for irradiation with an electromagnetic wave 1801 is a member of a cylindrical body having a bottom and an opening on the top surface of the cylindrical body. On the side wall (side surface) of the cup for irradiation with an electromagnetic wave 1801, an electromagnetic wave irradiating unit 1806 and an electromagnetic wave detecting unit 1807 are provided. The electromagnetic wave irradiating unit 1806 is connected to the oscillating unit 1803 to irradiate the opening of the cup for irradiation with an electromagnetic wave 1801 with the electromagnetic wave 1901. The electromagnetic wave detecting unit 1807 is connected to the detecting unit 1804 to detect the electromagnetic wave that enters the opening of the cup for irradiation with an electromagnetic wave 1801 and to transmit the electromagnetic wave to the detecting unit 1804.

The inside of the cup for irradiation with an electromagnetic wave 1801 is filled with a protection solution 1805. The electromagnetic wave from the electromagnetic wave irradiating unit 1806 reaches the opening through the protection solution 1805. Similarly, the electromagnetic wave passed through the object to be measured reaches the electromagnetic wave detecting unit 1807 from the opening through the protection solution 1805.

Figure 14:
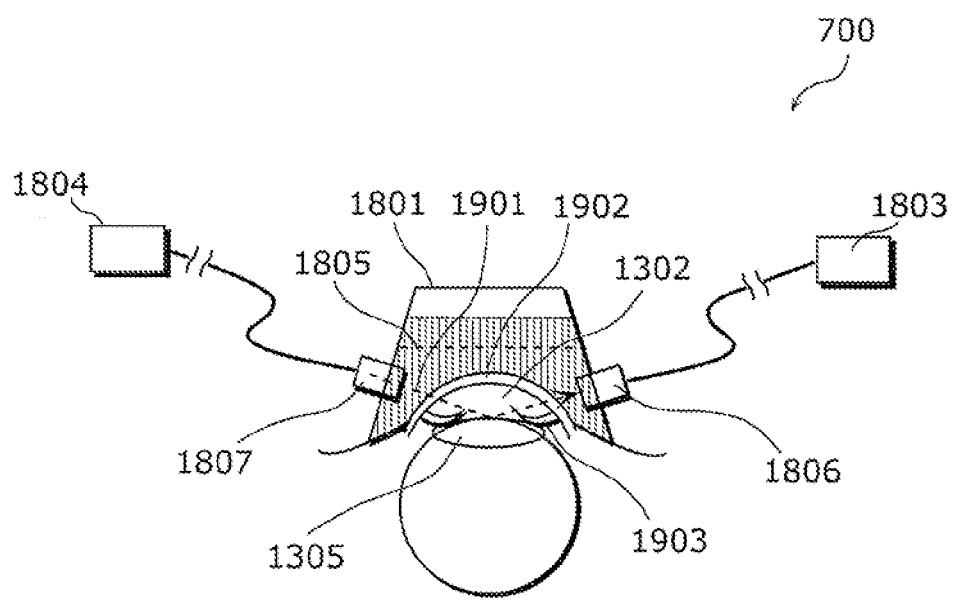
FIG. 14 is a drawing showing an example of use of the cup for irradiation with an electromagnetic wave.

Namely, in the state where the protection solution 1805 is filled up to a calibration marking 1802 inside of the cup for irradiation with an electromagnetic wave 1801, the cup is tightly pressed against an eye. In the state where a person to be measured turns up as it is so as not to spill the protection solution 1805 (state as shown in FIG. 14), the concentration of the target component is measured. Here, as the protection solution 1805, distilled water or normal saline can be used.

As shown in FIG. 14, the electromagnetic wave 1901 produced by the oscillating unit 1803 enters the inside of the cup for irradiation with an electromagnetic wave 1801 through the electromagnetic wave irradiating unit 1806. The electromagnetic wave 1901 that enters the cup for irradiation with an electromagnetic wave 1801 reaches a cornea 1902 through the protection solution 1805 with which the cup for irradiation with an electromagnetic wave 1801 is filled. The electromagnetic wave 1901 is reflected at a boundary between the anterior aqueous humor in an eye 1302 and the crystalline lens 1305, and reaches the electromagnetic wave detecting unit 1807 through the anterior aqueous humor in an eye 1302, the cornea 1902, and the protection solution 1805 again. The electromagnetic wave 1901 taken into the electromagnetic wave detecting unit 1807 is monitored by the detecting unit 1804.

In the component concentration meter that reflects the electromagnetic wave at a boundary having a small difference in the refractive index such as the boundary between the crystalline lens (refractive index 1.43) and the anterior aqueous humor in an eye (refractive index 1.33), and that between the anterior aqueous humor in an eye and the cornea (refractive index 1.37), the reflectance is small, and the output of the electromagnetic wave 1901 to reach the detecting unit 1804 is very small. For that reason, the reflectance is increased by increase in an angle of incidence to the reflecting surface. Thereby, an electromagnetic wave 1901 having a larger output can enter the detecting unit 1804, leading to a configuration with high accuracy as the component concentration meter 700.

In a configuration in which the electromagnetic wave 1901 enters the cornea 1902 through the air (refractive index 1), however, the angle of incidence to the boundary between the cornea 1902 and the anterior aqueous humor in an eye 1302 and that between the anterior aqueous humor in an eye 1302 and the crystalline lens 1305 is limited to approximately 46°.

For this reason, desirable is a configuration in which using the cup for irradiation with an electromagnetic wave 1801, the electromagnetic wave 1901 enters the cornea 1902 through the protection solution 1805. Thereby, an electromagnetic wave 1901 having a larger output reaches the detecting unit 1804, leading to improvement in the accuracy of the measurement as the component concentration meter 700.

More desirably, the protection solution 1805 having a refractive index of not less than 1.33 (refractive index higher than that of the anterior aqueous humor in an eye) is used. Thereby, the electromagnetic wave 1901 can enter the boundary between the anterior aqueous humor in an eye 1302 and the crystalline lens 1305 at any angle of incidence. In the case of the component concentration meter 700 that reflects the electromagnetic wave 1901 at the boundary, the concentration of the component can be measured more accurately.

Still more desirably, the protection solution 1805 having a refractive index of not less than 1.37 (refractive index higher than that of the cornea) is used. Thereby, the electromagnetic wave 1901 enters the boundary between the anterior aqueous humor in an eye 1302 and the cornea 1902 at any angle of incidence. Thereby, in the case of the component concentration meter 700 that reflects the electromagnetic wave 1901 at the boundary, the concentration of the component can be measured more accurately.

Desirably, except the electromagnetic wave irradiating unit 1806 and the electromagnetic wave detecting unit 1807, the cup for irradiation with an electromagnetic wave 1801 is composed of a highly light-shielding material. Alternatively, the cup for irradiation with an electromagnetic wave 1801 may be coated with a highly light-shielding coating. Thereby, the pupil (an exposed portion at the boundary between the crystalline lens and the anterior aqueous humor in an eye) is opened wider. Accordingly, alignment is easier in the configuration in which the electromagnetic wave 1901 is reflected at the boundary between the crystalline lens 1305 and the anterior aqueous humor in an eye 1302, or a configuration in which the blood vessel in the eyeground is irradiated with the electromagnetic wave 1901. As a result, a mechanism that adjusts the irradiation position of the eyeball with the electromagnetic wave 1901 can be simplified or eliminated, therefore providing a more inexpensive and compact component concentration meter.

In the case where using the phenomenon such as optical rotation and circular dichroism, the concentration of the component is measured based on the rotation angle of the polarized plane of the electromagnetic wave 1901, the measurement of the concentration of the component is more accurate as a difference between a distance of propagation of the electromagnetic wave 1901 in the anterior aqueous humor in an eye 1302 before reflection of the electromagnetic wave 1901 at the boundary between the crystalline lens 1305 and the anterior aqueous humor in an eye 1302 and that after reflection of the electromagnetic wave 1901 is larger.

For this reason, with the pupil being opened wider, the electromagnetic wave 1901 is reflected within the plane of the boundary between the crystalline lens 1305 and the anterior aqueous humor in an eye 1302 and at a position closer to an iris 1903. Thus, the concentration of the component can be measured more accurately.

Naturally, desirably, absorbance of electromagnetic wave 1901 by the protection solution 1805 is not changed according to the temperature. More desirably, the absorbance of the electromagnetic wave 1901 is small. Desirably, the protection solution 1805 does not demonstrate optical rotation and circular dichroism to the electromagnetic wave 1901. Thereby, the concentration of the component can be measured more accurately.

In the case where the electromagnetic wave 1901 is the near-infrared light, visible light, or ultraviolet light, an optical fiber may be used as the electromagnetic wave propagation path between the oscillating unit 1803 and the electromagnetic wave irradiating unit 1806 and that between the electromagnetic wave detecting unit 1807 and the detecting unit 1804.

Alternatively, the electromagnetic wave irradiating unit 1806 may be eliminated, and the oscillating unit 1803 may be directly attached to the side wall of the cup for irradiation with an electromagnetic wave 1801. Thereby, the concentration of the component can be measured more accurately.

Similarly, the electromagnetic wave detecting unit 1807 may be eliminated, and the detecting unit 1804 may be directly attached to the side wall of the cup for irradiation with an electromagnetic wave 1801. Thereby, a more compact component concentration meter can be provided, and cost can also be reduced.

In the case where the object to be measured is an object other than the eyeball, the concentration of the component may be measured by the configuration of FIG. 14 using the cup for irradiation with an electromagnetic wave 1801 and the protection solution 1805, instead of the depression projection smoothing material 107 shown in FIG. 4. Thereby, the measurement of the concentration of the component can be more accurately performed on the objects to be measured with a wider variety of shape.

As the electromagnetic wave for detection and the electromagnetic wave for heating, a terahertz wave at a wavelength of 30 µm to 3000 µm may be used. The terahertz wave has skeletal vibration of a polymer material, lattice vibration in the molecular structure, an absorbance property by bonding energy of local vibration, and the like. Thus, the terahertz wave has much information for distinguishing the substances, and is in the wavelength band in which the absorbance property largely changes according to the change in the temperature. Accordingly, use of the terahertz wave as the electromagnetic wave for detection enables more accurate measurement of the concentration particularly as the measurement of the concentration of the component in a polymer material.

In the case of using the terahertz wave, the oscillating unit may have a configuration as follows. For example, a chrome forsterite crystal is irradiated with YAG laser excitation light. The two generated waves are emitted onto a GaP crystal to generate a terahertz wave as difference frequency. Alternatively, a gas laser or a free electron laser may be used.

In the case where the oscillating unit is driven such that the electromagnetic wave for heating and the electromagnetic wave for detection both may have the waveform as shown in FIG. 5(*a*), desirably, a method in which in addition to the measurement time A and the measurement time B, the measurement under the same condition as that at the measurement time A and that at the measurement time B is repeated (measured at a measurement time A' and a measurement time B'), or measurement at a time (measurement time C) at which the temperature is a temperature between that at the measurement time A and that at the measurement time B is performed, and the measured values are used for calculation of the amount of glucose. If the number of times of the measurement is increased, a component concentration meter with higher accuracy can be provided.

As above, in Embodiments 1 to 5, the component concentration meter according to the present invention has been described in which the concentration of glucose is measured using the blood vessel of a finger or the anterior aqueous humor in an eye as the object to be measured. Herein, however, the configurations shown in the embodiments are only an example, and various modifications can be made without departing the scope of the present invention. Additionally, the followings hold true concerning Embodiments 1 to 5.

First, in order to measure the concentration of glucose in the blood in the same manner as in the examples shown in the five embodiments above, the blood vessel of an ear may be used as the object to be measured. Use of a thin object to be measured such as the ear can reduce a sensitivity necessary for the detecting unit, leading to a more inexpensive component concentration meter.

In the case where more inexpensive measurement of the blood sugar level is demanded, an eardrum is desirably used as the object to be measured. The structure of the eardrum has a flat and uniform surface. Accordingly, the accuracy for calculation of the amount of the temperature to be increased can be improved, leading to the measurement of the concentration of glucose with high accuracy.

In the case where the measurement of the concentration of glucose with high accuracy is demanded, desirable is a configuration including a vein identifying device to prevent deviation of the position to be measured for each measurement. The accuracy of the measurement can be further improved.

Alternatively, an exhaled breath condensate prepared by cooling an exhaled breath may be used as the object to be measured. Similarly to the anterior aqueous humor in an eye, the exhaled breath condensate can reduce the measurement errors caused by scattering or the like, leading to the measurement of the concentration of glucose with higher accuracy. For this reason, use of the exhaled breath condensate as the object to be measured can provide a more inexpensive component concentration meter.

Alternatively, a method may be used in which the blood vessel of the eyeground may be irradiated with the electromagnetic wave; then, the electromagnetic wave may be reflected to be guided to the detecting unit. Use of the blood vessel of the eyeground as the object to be measured can reduce scattering of the electromagnetic wave by the skin or the like. Accordingly, the intensity of the light in the blood as the object to be measured can be adjusted with high accuracy. Thereby, the accuracy of the measurement of the concentration of glucose can be improved. For this reason, the non-invasive measurement of the concentration of glucose with highest accuracy can be provided. The blood vessel of the eyeground is desirably used as the object to be measured.

In the case where using the earlobe, the skin, or the anterior aqueous humor in an eye as the object to be measured, the concentration of glucose is measured, the propagation path of the electromagnetic wave for detection within the object to be measured has a length of not less than 1 mm. Particularly, in the case of the skin as the object to be measured, desirably, the electromagnetic wave for detection and the electromagnetic wave for heating both reach the dermis 2 to 3 mm deeper than the skin surface. Thereby, the blood sugar level can be measured more accurately.

In order to heat the propagation path having a length of not less than 2 mm more uniformly, the electromagnetic wave for heating desirably has a wavelength of 1450 nm to 1850 nm. Thereby, the concentration of the component can be measured more accurately.

In addition, desirably, the absorbance electromagnetic wave for heating by the object to be measured is not changed according to the change in the temperature. In the case where the electromagnetic wave for detection has a different wavelength from that of the electromagnetic wave for heating, the wavelength of the electromagnetic wave for heating is most desirably 1450 nm to 1600 nm. Thereby, the concentration of the component can be measured more accurately.

Desirably, the electromagnetic wave for detection is the linearly polarized wave, and a device that rotates the polarization direction of the electromagnetic wave is provided between the oscillating unit and the object to be measured. Thereby, in addition to the amount of the transmittance to be changed of the object to be measured accompanied by change in the temperature, the polarization dependency can be used as a parameter to determine the concentration of the target component, leading to more accurate measurement of the concentration of the component. The same effect can also be demonstrated if a method is used in which the electromagnetic wave for detection is a circularly polarized wave or random polarized wave, and a rotary polarized wave separator is provided between the object to be measured and the detecting unit.

Desirably, the electromagnetic wave for detection is the linearly polarized wave, it is configured so as to determine the polarization component of the electromagnetic wave emitted from the object to be measured, and an electric field generating unit that applies an electric field to the electromagnetic wave propagation path parallel to the propagation direction of the electromagnetic wave in the electromagnetic wave propagation path is provided. Thereby, magnetic dichroism can be used for the measurement of the concentration of the component, and the concentration of the component having magnetic dichroism can be measured with high accuracy.

In the case where the electromagnetic wave for heating is in the near-infrared range, visible light range, or ultraviolet range, desirably, a rod integrator or a fly-eye lens, not illustrated, is provided in the electromagnetic wave propagation path between the oscillating unit and the object to be measured to reduce unevenness of the intensity of the electromagnetic wave within the object to be measured. As unevenness of the intensity of the magnetic wave the electromagnetic wave for heating within the object to be measured is further reduced, fluctuation in the amount of the temperature of the object to be measured to be increased according to a place within the object to be measured is more suppressed, and the accuracy of the measurement can be further enhanced.

The electromagnetic wave for heating is absorbed by the object to be measured, and attenuates according to the distance of propagation as the electromagnetic wave for heating propagates within the object to be measured. For this reason, desirably, in order to increase the uniformity of the intensity of the electromagnetic wave in the propagation direction, the converging lens 108 (see FIG. 4) that converges the electromagnetic wave is provided. Desirably, the converging position of the electromagnetic wave is behind the object to be measured in the propagation direction. Thereby, fluctuation in the intensity of the electromagnetic wave in the propagation direction is reduced, providing a component concentration meter with higher accuracy.

As an embodiment of the present invention, 2-cycle pulse driving of the oscillating unit as shown in FIG. 5(*a*) to FIG. 5(*c*) is not a condition essential to the present invention, and at least one output and change may be sufficient.

Desirably, the oscillating unit (at least the oscillating unit for heating in the case where the electromagnetic wave for heating is oscillated by one oscillating unit and the electromagnetic wave for detection is oscillated from other oscillating unit) is pulse driven at a different pulse energy. Here, the pulse energy is a value represented by a product of the amplitude of the electromagnetic wave pulse and the irradiation time.

Figure 15:
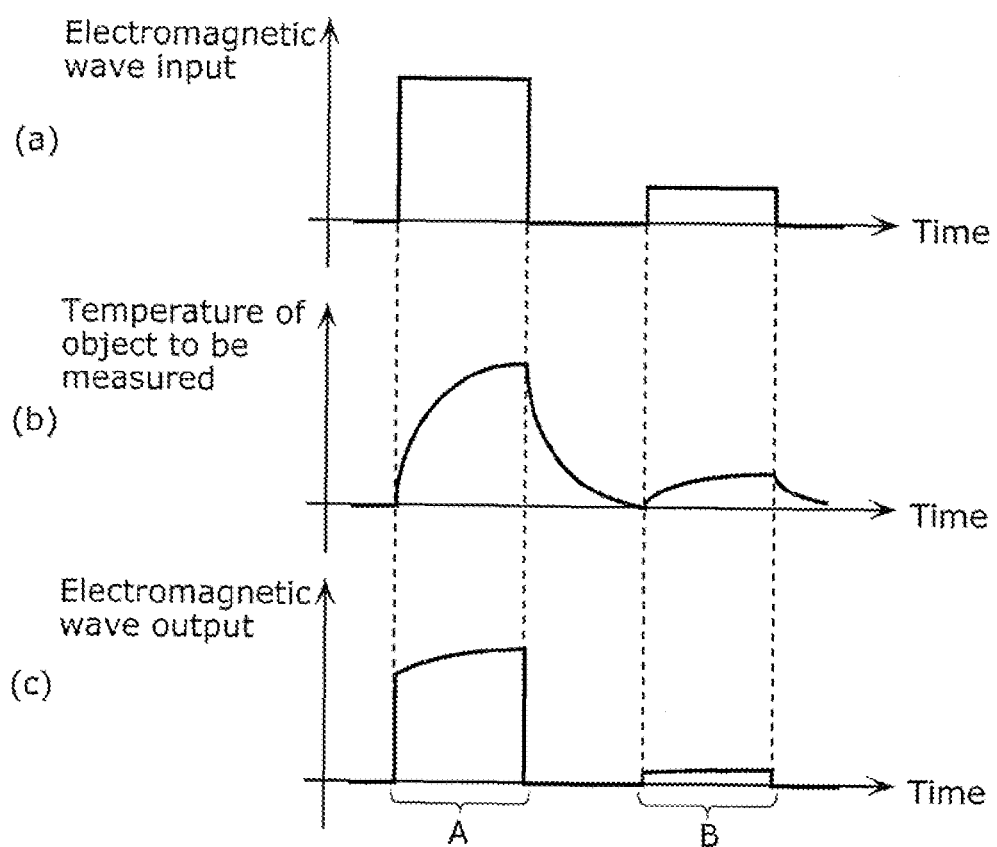
FIG. 15 is (a) a drawing showing an example of a waveform of an electromagnetic wave input to an object to be measured, (b) a drawing showing an example of change in the temperature of the object to be measured, and (c) a drawing showing an example of a waveform of an electromagnetic wave output from the object to be measured.

For example, the oscillating unit may irradiate the object to be measured with a high output pulse and a low output pulse as shown in FIG. 15(*a*). Namely, the oscillating unit may irradiate the object to be measured with two electromagnetic wave pulses each having a different pulse energy by varying a peak power between the first and second electromagnetic wave pulses In this case, as shown in FIG. 15(*b*), increase in the temperature of the object to be measured at irradiation with the low output pulse is smaller than that at irradiation with the high output pulse. For this reason, as shown in FIG. 15(*c*), the entire period of irradiation time with the high output pulse is a measurement period of time A, and the entire period irradiation time with the low output pulse is a measurement period of time B. The average values of the transmittances in the two measurement periods of time (average transmittance) are compared to determine the amount of glucose. Use of the method can provide highly accurate measurement of the concentration of the component even if a detecting unit having low time resolution (response speed of µs or more) is used, and is desirable. Thereby, a more inexpensive detecting unit can be selected.

Figure 16:
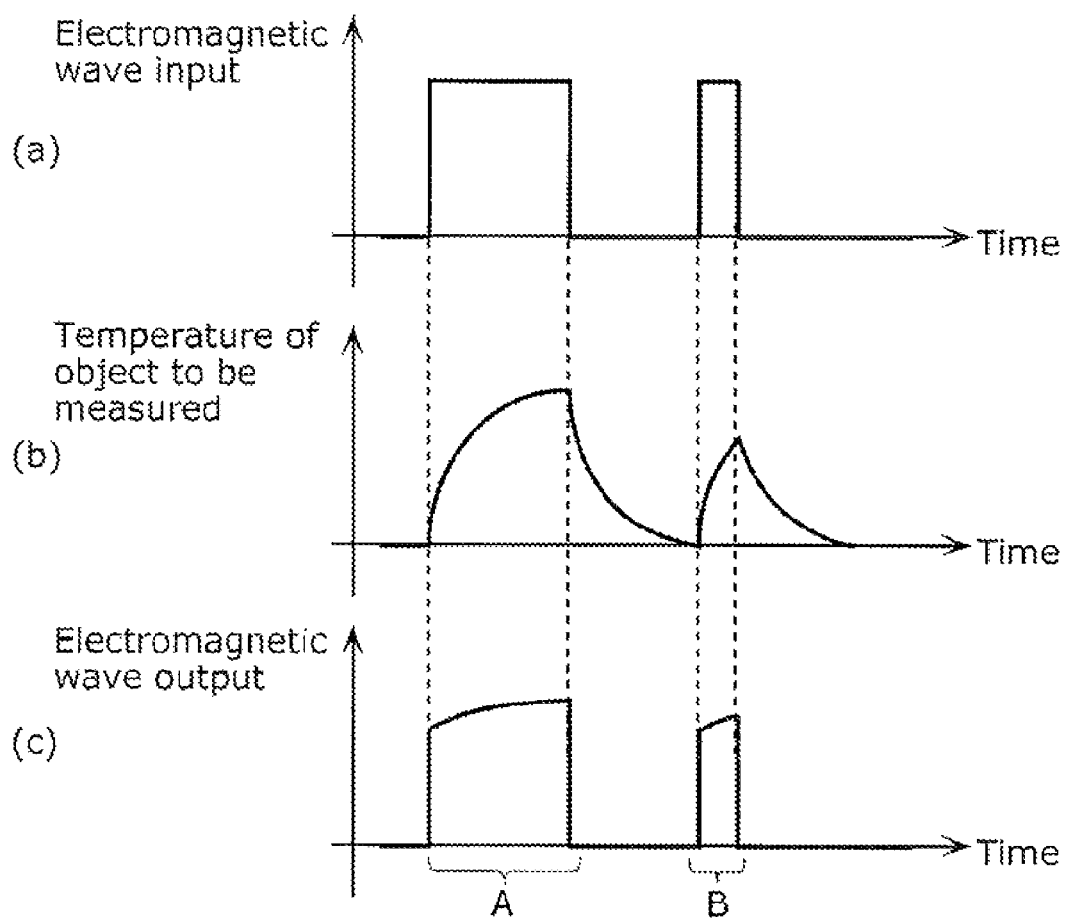
FIG. 16 is (a) a drawing showing an example of a waveform of an electromagnetic wave input to an object to be measured, (b) a drawing showing an example of change in the temperature of the object to be measured, and (c) a drawing showing an example of a waveform of an electromagnetic wave output from the object to be measured.

Alternatively, the oscillating unit (both of the oscillating unit for heating and that for detection) may be pulse driven at a different pulse width. For example, the oscillating unit may irradiate the object to be measured with a long pulse and a short pulse as shown in FIG. 16(*a*). Namely, the oscillating unit may irradiate the object to be measured with two electromagnetic wave pulses each having a different pulse energy by varying an irradiation time with the electromagnetic wave pulse between the first and second electromagnetic wave pulses.

In this case, as shown in FIG. 16(*b*), increase in the temperature of the object to be measured at irradiation with the short pulse is smaller than that at irradiation with the long pulse. For this reason, as shown in FIG. 16(*c*), the entire period of irradiation time with the long pulse is a measurement period of time A, and the entire period of irradiation time with the short pulse is a measurement period of time B. The average transmittances in the two measurement periods of time are compared to determine the amount of glucose. Use of the method can provide highly accurate measurement of the concentration of the component even if a detecting unit having a low time resolution (response speed of the order of μs or more) such as a thermal sensor is used. Thereby, a more inexpensive detecting unit can be selected. Use of a thermal sensor enables highly accurate measurement.

Further, in the method, the peak output of the long pulse is the same as that of the short pulse. Accordingly, even if the object to be measured having a nonlinear absorption property such as two-photon absorption is detected, reduction in the accuracy of the measurement due to the influence can be suppressed.

Figure 17:
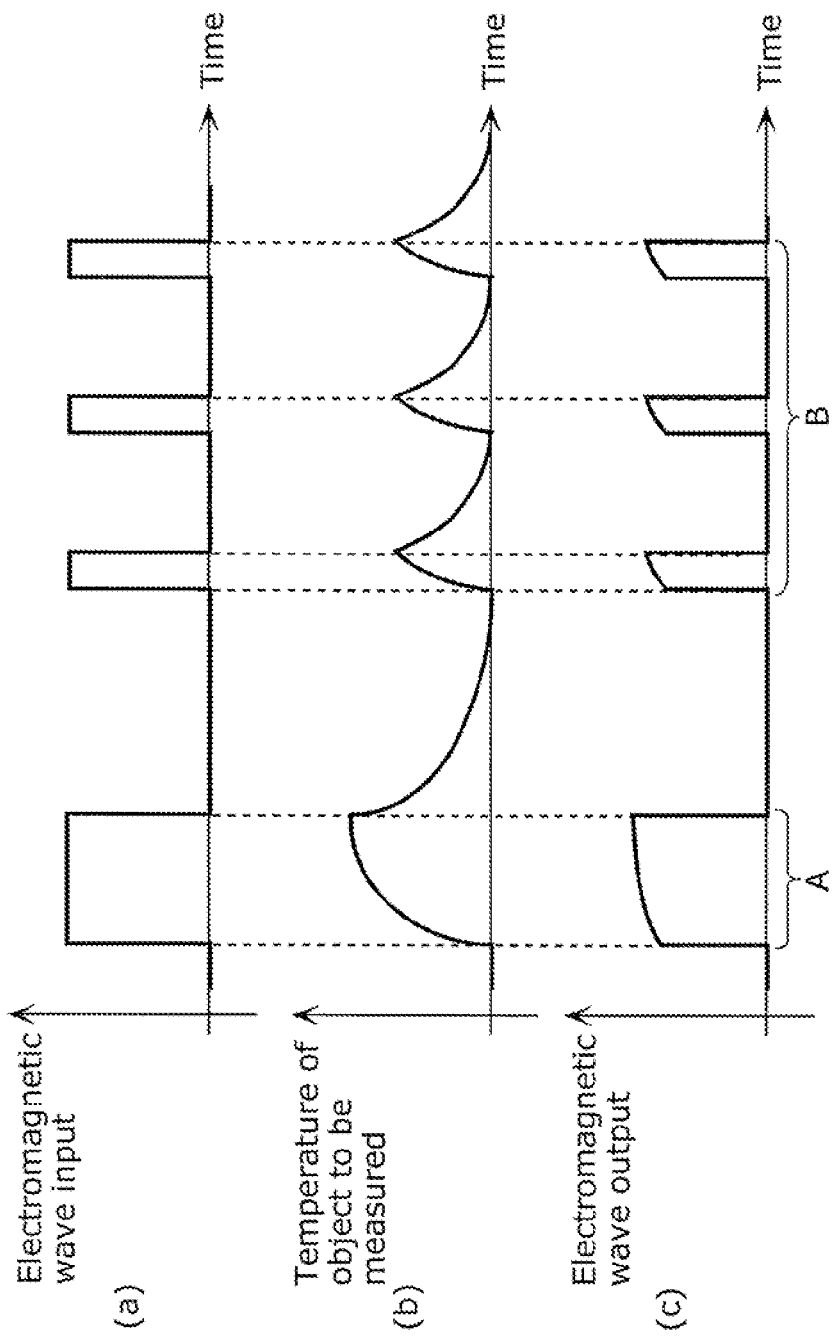
FIG. 17 is (a) a drawing showing an example of a waveform of an electromagnetic wave input to an object to be measured, (b) a drawing showing an example of change in the temperature of the object to be measured, and (c) a drawing showing an example of a waveform of an electromagnetic wave output from the object to be measured.

Alternatively, the oscillating unit (both of the oscillating unit for heating and that for detection) may be pulse driven at a different pulse width to irradiate the object to be measured with the long pulse and a plurality of continuous short pulses as shown in FIG. 17(a). In this case, as shown in FIG. 17(b), increase in the temperature of the object to be measured at irradiation with the plurality of continuous short pulses is smaller than that at irradiation with the long pulse. For this reason, as shown in FIG. 17(c), the entire period of irradiation time with the long pulse is a measurement period of time A, and the entire period of irradiation time with the plurality of continuous short pulses is a measurement period of time B. The average transmittances in the two measurement periods of time are compared to determine the amount of glucose. This method is particularly desirable in the case where a detecting unit at a response speed of the order of seconds having a low sensitivity such as a thermal sensor is used. Namely, even use of the thermal sensor enables much more accurate measurement of the concentration of the component than in the case where the transmittance of a single long pulse is compared with that of a single short pulse.

In the case where the present invention is used to measure the concentration of the blood sugar, the blood is desirably increased several degrees or more instantaneously. For that, irradiation with the electromagnetic wave pulse at not less than 2 mJ and not more than 8 mJ is desirable. This can cause larger change in the transmittance, improving the accuracy of the measurement of the concentration of the component.

Desirably, the pulse width of the electromagnetic wave is several ms or less. The pulse width at several ms can prevent waste of the energy needed for heating because the heated blood moves outside of a measurable area. Thereby, a component concentration meter with lower power consumption, and a compact component concentration meter can be achieved.

The component concentration meter according to the present invention desirably includes a device that measures the temperature of the object to be measured. Thereby, the amount of the temperature to be changed can be measured more accurately. For this reason, the amount of glucose can be measured with high accuracy.

Alternatively, the device that measures the temperature of the object to be measured may be a device using a photoacoustic effect or a device using an electromagnetic wave. Thereby, a more compact component concentration meter can be provided.

Alternatively, a device that measures the thermal conductivity and heat capacity of the object to be measured may be provided to expect the temperature of the object to be measured. In this case, a method is more desirable in which the electromagnetic waves each having a different beam diameter, pulse waveform, and wavelength enter the object to be measured, and the thermal conductivity and heat capacity are determined from the change in the transmittance. Thereby, more fast measurement of the concentration of the component can be provided.

Alternatively, a method may be used in which the amount of the temperature to be increased is thermal analytically analyzed from the absorptivity of the electromagnetic wave (the amount of heat to be produced by the electromagnetic wave) of the object to be measured and the heat capacity and thermal conductivity of the object to be measured. The absorptivity of the electromagnetic wave can be determined from the transmittance of the electromagnetic wave. This method can determine the temperature without a device for measuring a temperature, leading to reduction in cost of the component concentration meter.

If of the substances contained in the object to be measured, there is a substance having an already known concentration, using a wavelength at which the absorptivity by the substance changes according to the change in the temperature of the substance, the amount of the temperature of the object to be measured to be changed can be determined. Namely, the substance within the object to be measured whose concentration is known is X, and the concentration of X is Cx. The difference in the transmittance according to the change in the temperature at a wavelength at which the absorptivity of X changes according to the change in the temperature is ΔTx.

Here, ΔTx is proportional to the product of Cx and the amount of the change in the temperature. For this reason, if the proportional constant is determined in advance, the amount of the change in the temperature can be determined from ΔTx. Similarly, the target component is Y, the concentration of Y is Cy, and the difference in the transmittance according to the change in the temperature at a wavelength at which the absorptivity by Y changes according to the change in the temperature is ΔTy. ΔTy is also proportional to the product of Cy and the amount of the change in the temperature. For this reason, if the proportional constant is determined in advance, Cy can be determined from ΔTy and the amount of the change in the temperature determined here.

According to the description above, in the case where in the other components than the target component contained in the object to be measured, there is no substance equivalent to X whose concentration in the object to be measured is known, a substance (Z) having the absorptivity to be changed according to the change in the temperature is desirably mixed instead of X. Thereby, even if there is no X whose concentration in the object to be measured is known, the concentration can be measured with high accuracy.

Desirably, the mass of the object to be measured and the mass of Z are measured in advance. Thereby, the concentration of the component in Z contained in the object to be measured is determined with higher accuracy. Accordingly, the amount in the change in the temperature and the concentration of the target component are also determined with higher accuracy.

In the case of the component concentration meter in the blood or in the anterior aqueous humor in an eye, water is desirably used as X. Similarly to the case of glucose, the concentration of the component contained is known in advance, and the amount of the change in the temperature can be determined using an electromagnetic wave at a wavelength at which the absorptivity by a substance other than water in the blood is small. Accordingly, the amount of the change in the temperature and the concentration of glucose can be determined with higher accuracy.

In the case where the component concentration meter according to the present invention is used for an apparatus for measuring a concentration of blood sugar, the amount in the change (increase) in the temperature is proportional to the production of the intensity of the electromagnetic wave and the concentration of glucose, although the proportionality constant is varied depending on individuals. For this reason, desirably, in the state where the concentration of glucose is known in advance (the state where the concentration of glucose is measured by other method such as extraction of the blood), the relationship between the difference between the transmittance at the measurement time A and that at the measurement time B and the concentration of glucose is created into a table. Thereby, based on the table, the amount of glucose can be deduced from the difference in the transmittance. Creation of the table can provide the measurement of the concentration of the target component with higher accuracy.

In Embodiments 1 to 5, the electromagnetic wave is used as the device that heats the object to be measured. Using other device such as a heater and a Peltier device, the object to be measured may be heated or cooled. If the heating device and the cool device are an electromagnetic wave, the object to be measured can be locally heated in the propagation path of the electromagnetic wave for detection, and the temperature of the object to be measured can be increased more rapidly. For this reason, the measurement time can be reduced. In addition, reduction in the heating time and measurement time can provide larger change in the temperature without denaturing the biological cells, and improve the accuracy of the measurement of the concentration of the component.

Desirably, the absorptivity of the electromagnetic wave for heating by glucose is as large as possible, and that by other component than glucose contained in the object to be measured is as small as possible. Thereby, the difference in the concentration of glucose influences the change in the transmittance more largely because the amount of increase in the temperature of the object to be measured depends on the concentration of glucose. As a result, the concentration of glucose can be measured with higher accuracy.

In Embodiments 1 to 5, desirably, the concentration of the component is measured as follows: the object to be measured is cooled in advance to evaluate the transmittance, optical rotation, circular dichroism, and the like; after heating of the object to be measured, the transmittance, optical rotation, circular dichroism, and the like are evaluated to be compared with those before heating. Even if the object to be measured is an object to be measured whose substance is denatured due to a high temperature, such as an animal or a plant, error measurement caused by denaturing can be prevented. Additionally, a wider range of the change in the temperature can improve the accuracy of the measurement.

More desirably, the concentration of the component is measured by a method in which a table showing photoabsorptivity for each component at a plurality of temperatures and dependency of circular dichroism on the wavelength is prepared; a plurality of electromagnetic waves each having a different wavelength is used as the electromagnetic wave for detection; the transmission spectrum and dependency of circular dichroism on the wavelength are measured at a plurality of temperatures to perform the multivariate analysis. Thereby, the concentration of a plurality of components can be analyzed at the same time with high accuracy.

The component concentration meter that measures the concentration of glucose has been described above. The component concentration measurement method according to the present invention can be applied to measurement of the concentration of the target component contained in other object to be measured than above. The same effect can be obtained with the same configuration as that shown in Embodiments 1 to 5.

For example, in the case where the component concentration meter according to the present invention is used for measurement of the concentration of moisture in an object to be measured containing moisture, the near-infrared light having a wavelength of not less than 1100 nm and not more than 1180 nm or a wavelength of not less than 900 nm and not more than 990 nm is used as the electromagnetic wave for detection. Thereby, the measurement of the concentration of the component according to the present invention can be performed based on the change in the transmittance of the electromagnetic wave transmittance according to the change in the temperature.

In use for measurement of the concentration of protein, the visible light having a wavelength of not less than 560 nm and not more than 770 or the ultraviolet light having a wavelength of not less than 260 nm and not more than 290 nm is used. Thereby, similarly, the measurement of the concentration of the component according to the present invention can be performed, based on the change in the transmittance of the electromagnetic wave transmittance according to the change in the temperature.

Hereinafter, the embodiments of the component concentration meter according to the present invention for other purpose than measurement of the concentration of the target component in the blood will be described.

Embodiment 6

Figure 18:
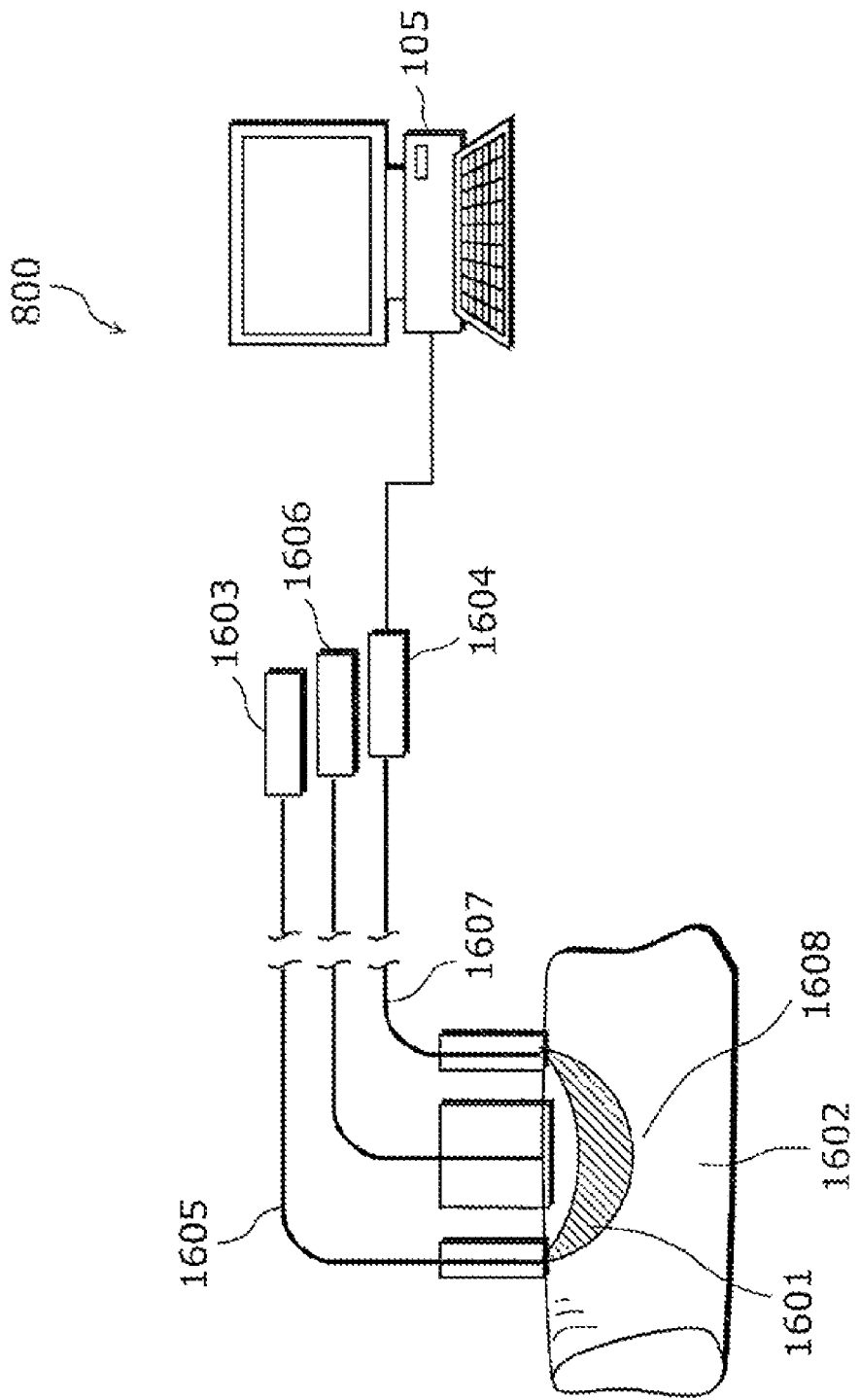
FIG. 18 is a drawing showing a schematic configuration of a component concentration meter according to Embodiment 6 of the present invention.

FIG. 18 is a drawing showing a schematic configuration of a component concentration meter 800 according to Embodiment 6 of the present invention. In Embodiment 6, the component concentration meter 800 that measures the concentration of protein contained in a frozen mashed meat (fish meat) as an example of the object to be measured will be described. Detailed description of the same parts as those in Embodiments 1 to 5 will be omitted, and the differences will be mainly described. Same reference numerals are given to the same components as those in Embodiments 1 to 5.

As shown in FIG. 18, the component concentration meter 800 according to the present embodiment includes oscillating units 1603 and 1606, optical fibers 1605 and 1607, a detecting unit 1604, and a computing unit 105. The component concentration meter 800 guides an electromagnetic wave 1601 oscillated by the oscillating unit 1603 to a frozen mashed meat 1602. Here, the electromagnetic wave 1601 has a wavelength in the range of the near-infrared light to the ultraviolet light, and is guided to the frozen mashed meat 1602 using the optical fiber 1605.

The other optical fiber 1607 contacts the surface of the frozen mashed meat 1602 in the vicinity of the place where the optical fiber 1605 is provided. Thereby, part of the electromagnetic wave 1601 scattered within the frozen mashed meat 1602 enters the optical fiber 1607 to be guided to the detecting unit 1604.

In the present embodiment, as the electromagnetic wave 1601, the visible light having a wavelength of not less than 560 nm and not more than 770 or the ultraviolet light having a wavelength of not less than 260 nm and not more than 290 nm may be used, for example. The absorbance of the light at these wavelengths is particularly largely changed according to the change in the temperature of the protein. Accordingly, the concentration of the component can be measured with higher accuracy.

In the present embodiment, the same effect can be obtained by the same method as in Embodiments 1 to 5, although the object to be measured and the target component are different from those in Embodiments 1 to 5. For example, the oscillating unit 1603 is driven so as to provide a waveform as shown in FIG. 5(*a*), and the concentration of the component is measured according to the flowchart shown in FIG. 6 to provide the same effect as that in Embodiment 1. (Here, similarly to Embodiment 1, the electromagnetic wave 1601 is used as both of the electromagnetic wave for heating and the electromagnetic wave for detection.)

Similarly to Embodiment 2, the component concentration meter 800 may further include an oscillating unit 1606 that oscillates an electromagnetic wave 1608 for heating. The electromagnetic wave 1601 may be used as the electromagnetic wave for detection, and the electromagnetic waves 1601 and 1608 may be arranged so as to be overlaid within the frozen mashed meat 1602. With the configuration, the oscillating units 1603 and 1606 are driven such that the electromagnetic wave for heating and the electromagnetic wave for detection both may have the waveform as shown in FIG. 5(*a*), and the concentration of the component is measured according to the flowchart shown in FIG. 6. Thus, the same effect as in Embodiment 2 can be obtained.

In the present embodiment, similarly to Embodiment 2, the amount of protein can be determined from the difference in the transmittance measured several times using the pump-probe method. Desirable is the measurement of the concentration of the component using both of the change in the transmittance of the electromagnetic wave according to the change in the temperature and the recovery rate from saturated absorption. Thereby, a component concentration meter with higher accuracy can be provided.

Desirably, the optical fiber 1605 and the optical fiber 1607 are formed into one bundle fiber. Thereby, an interval between the position at which the optical fiber 1605 contacts the frozen mashed meat 1602 and that at which the optical fiber 1607 contacts the frozen mashed meat 1602 is constant, providing a constant propagation distance of the electromagnetic wave 1601 within the frozen mashed meat 1602. For this reason, the concentration of the component can be measured more accurately.

In the case where with the same configuration as that in the present embodiment, the object to be measured is the skin of a human body, and the concentration of glucose in the blood is measured, the position at which the optical fiber 1605 contacts the skin is desirably spaced not less than 0.5 mm from the position at which the optical fiber 1607 contacts the skin. Thereby, after the electromagnetic wave 1601 is emitted from the optical fiber 1605, the electromagnetic wave 1601 passed through the dermis is taken into the optical fiber 1607. For this reason, a component concentration meter with high accuracy can be provided.

Desirably, a plurality of optical fibers that takes in the electromagnetic wave 1601 scattered within the frozen mashed meat 1602 to guide the electromagnetic wave 1601 to the detecting unit 1604 is provided. Thereby, larger part of the electromagnetic wave 1601 can be guided to the detecting unit 1604, leading to the measurement of the concentration of the component with higher accuracy.

In the present embodiment, in the configuration in which the object to be measured is irradiated with the electromagnetic wave for heating and the electromagnetic wave for detection, the optical fiber as shown in FIG. 18 is not always necessary. In the case of the object to be measured with much scattering, the configuration as shown in FIG. 18 can provide high accuracy in the measurement. According to the object to be measured, the optical configurations in the component concentration meters shown in Embodiments 1 to 5 may be used. The same configuration can provide the same effect.

In some cases, the optical configurations in the component concentration meters shown in the Embodiments 1 to 4 are more desirable. For example, using a converging optical system, the electromagnetic wave for heating is converged into several hundreds μm or less, and the frozen mashed meat is irradiated with the converged electromagnetic wave for heating. Thereby, only a limited portion of the frozen mashed meat can be heated. For this reason, the concentration of the protein can be measured without thawing the frozen mashed meat 1602, unlike the case where the electromagnetic wave that cannot be converged into several hundreds μm or less such as a microwave or a heater is used for heating. In this case, the short pulse light having a wavelength of several hundreds μm or less is desirably used as the electromagnetic wave for heating. Thereby, the size of the converging optical system can be reduced.

In all the cases where the object to be measured is not only the frozen mashed meat but also a frozen food and the concentration of the target component within the object to be measured is measured, the short pulse light is desirably converged into several μm or less to heat the object to be measured for the same reason.

In the case where the object to be measured is other than a frozen food and heating thereof is not desirable, the short pulse light is desirably converged into several hundreds μm or less to heat the object to be measured for the same reason.

Particularly, in the case where the object to be measured is a food or a living body such as a human body as shown in Embodiments 1 to 5, the pulse width is desirably not more than 1 μs. Thereby, the heat action to the biological cells can be significantly reduced.

In the case where the object to be measured is a food or a living body, the pulse width of the electromagnetic wave for irradiation is desirably not less than 10 ns. Thereby, occurrence of photoablation can be prevented, and the object to be measured can be pulse heated.

In these cases, desirably, the electromagnetic wave for detection is converged into several hundreds μm or less so as to be directed within the irradiation area of the electromagnetic wave for heating, and the object to be measured is irradiated with the converged electromagnetic wave for detection in the same manner. Thereby, the difference in the temperature across the entire transmitting portion of the electromagnetic wave for detection can be suppressed, leading to improvement in the accuracy of the measurement.

Embodiment 7

Figure 19:
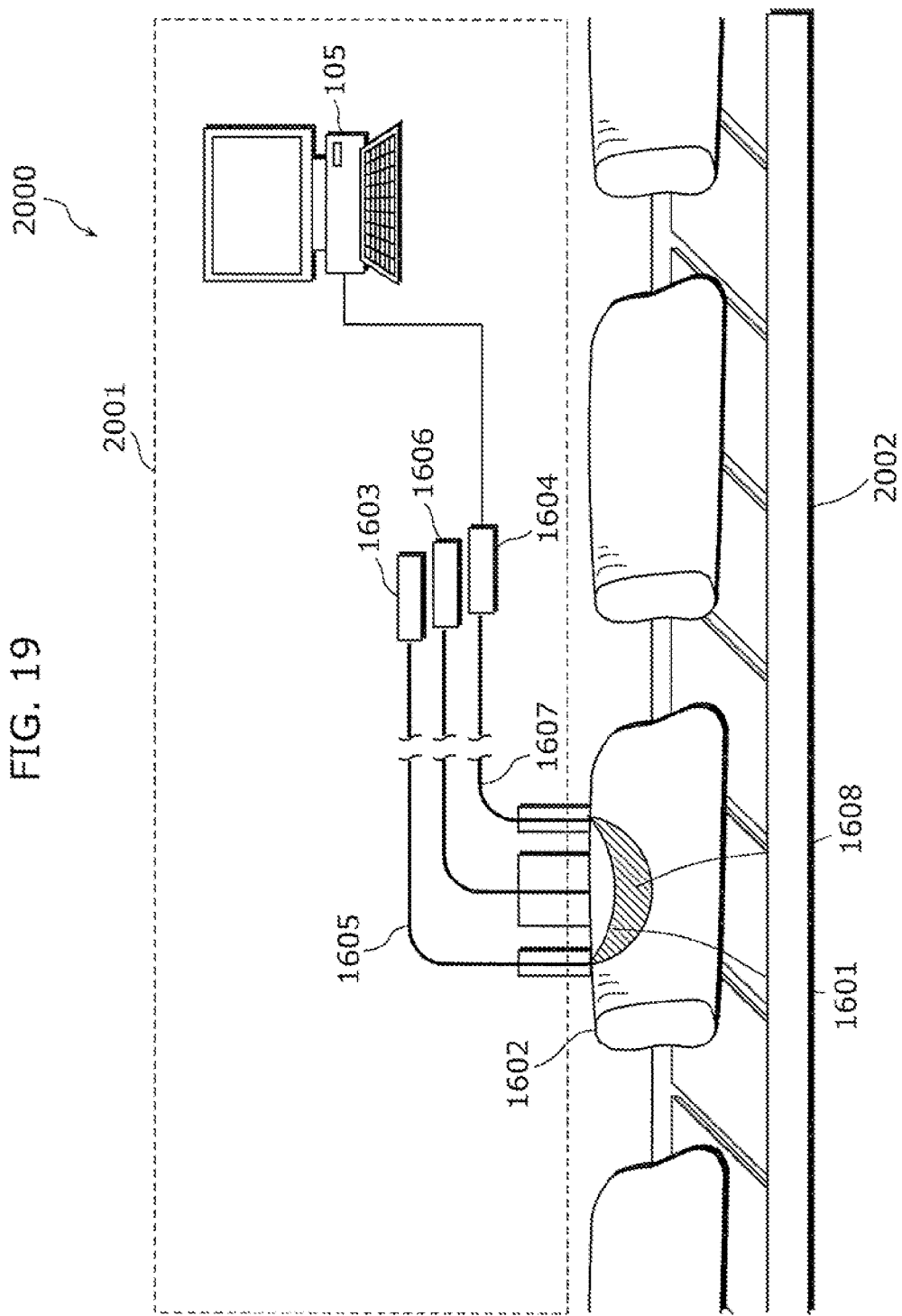
FIG. 19 is a drawing showing a schematic configuration of a shipping inspection system according to Embodiment 7 of the present invention.

FIG. 19 is a drawing showing a schematic configuration of a shipping inspection system 2000 according to Embodiment 7 of the present invention. Detailed description of the same parts as those in Embodiments 1 to 6 will be omitted, and the differences will be mainly described. Same reference numerals are given to the same components as those in Embodiments 1 to 6.

As shown in FIG. 19, the shipping inspection system 2000 according to the present embodiment includes a component concentration meter 2001 that measures the concentration of the protein contained in a frozen mashed meat (fish meat), and a conveyor belt (conveyor) 2002. The component concentration meter 2001 may have the same configuration as that of the component concentration meter 800 according to Embodiment 6.

The frozen mashed meat 1602 is conveyed by the conveyor belt 2002. At an instance when each frozen mashed meat 1602 transmits through a position (measurement position) at which the frozen mashed meat is irradiated with the electromagnetic waves 1601 and 1608 emitted from the oscillating units 1603 and 1606, respectively, the concentration of the protein contained in the frozen mashed meat 1602 is measured.

Here, the component concentration meter 800 shown in Embodiment 6 is used. An shipping inspection system with higher accuracy can be provided using the component concentration meter according to the present invention having other configuration of the component concentration meter shown in other Embodiments.

Here, an example of the shipping inspection system that measures the concentration of the protein contained in the frozen mashed meat has been shown. The same configuration can provide a system that inspects a variety of foods or chemicals.

For example, the component concentration meter having the same configuration can measure the concentration of the component with higher accuracy in measurement of the concentration of a pesticide residue such as Malachite green or poison such as arsenic mixed in a food. In these applications, use of the short pulse electromagnetic wave for heating the object to be measured can lead to the measurement of the concentration of the target component without thawing even if the object to be measured is a frozen food.

In the case where Malachite green is the target component, the visible light having a wavelength 520 nm to 720 nm is desirably used as the electromagnetic wave for detection and the electromagnetic wave for heating. Thereby, the concentration of Malachite green can be measured with high accuracy.

As described above, the component concentration meter according to the present invention is desirably used for the shipping inspection system. The concentration of a component can be fast measured with high accuracy without thawing a frozen food if the object to be measured is the frozen food. Thereby, all the products in-line in a food process factory can be inspected.

The component concentration meter according to the present invention can be used for a calorimeter as an example of a health management system to measure the concentrations of a plurality of components contained in a food such as sugar, fat, and protein, and calculate the calorie contained in the food. If the calorie of each food is measured, the calorie of the food can be displayed more accurately. Other application of the calorimeter than shipping inspection can also be thought. For example, the amount of the calorie to be taken can be controlled in hospitals, nursing homes, and households.

Such a health management system includes one of the component concentration meters according to Embodiments 1 to 5 that calculate the respective concentrations of a plurality of components contained in the object to be measured, and a calorie calculating unit configured to calculate the calorie of the object to be measured based on the respective concentrations of the plurality of components calculated by the component concentration meter, for example.

The saccharides are classified into components such as glucose, fructose, trehalose, and maltose more in detail, and the concentrations of the respective components are measured. Thereby, the health management system can be used as a sweetness measuring system that calculates "sweetness" as an example of the health management system. The measurement of the sugar content is already performed as shipping inspection of fruits such as peaches. If the component concentration meter according to the present invention is used to calculate an additional index of the "sweetness," the value of the product can be measured more accurately.

Such a health management system includes one of the component concentration meters according to Embodiments 1 to 5 that calculates the respective concentrations of several kinds of saccharides contained in the object to be measured, and a sweetness calculating unit configured to calculate the sweetness of the object to be measured based on the respective concentrations of the several kinds of saccharides calculated by the component concentration meter, for example.

Trehalose and maltose are digested faster than other starch sugars, and are likely to cause obesity. Then, a health management system may be provided in which the obesity coefficient of each component is determined, and the obesity coefficient of each component is multiplied by the concentration to calculate an index of the "obesity" for each food. Thereby, a device for preventing lifestyle-related diseases caused by the obesity can be provided.

The health management system may have function to propose a desirable food material to be taken or a food menu using the food material in addition to the index. The health management system may also have function to propose a time to have the next meal based on the digestion speeds of the respective components contained in the food. These functions assist in a healthier dietary life.

Similarly, a shipping inspection system using the component concentration meter according to the present invention is desirably used in pharmaceutical plants and pharmacies as a check test after preparation of a test reagent or a purity test. The shipping inspection system according to the present invention can measure the proportion of each component to be mixed contained in the test reagent to prevent a mistaken formulation of a drug or mixture of foreign substances. The non-contact shipping inspection system can also inspect all the products fast.

Embodiment 8

Figure 20:
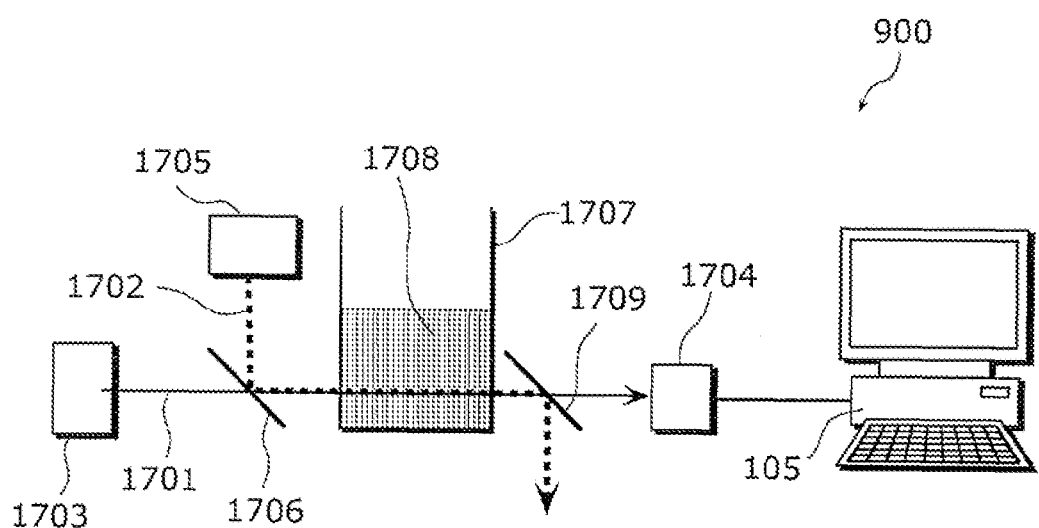
FIG. 20 is a drawing showing a schematic configuration of a component concentration meter according to Embodiment 8 of the present invention.

FIG. 20 is a drawing showing a schematic configuration of a component concentration meter 900 according to Embodiment 8 of the present invention. In Embodiment 8, the component concentration meter 900 that measures the concentration of the ammonium ion as the target component contained in an aqueous solution as the object to be measured will be described. Detailed description of the same parts as those in Embodiments 1 to 7 will be omitted, and the differences will be mainly described. Same reference numerals are given to the same components as those in Embodiments 1 to 7.

As shown in FIG. 20, the component concentration meter 900 according to the present embodiment includes oscillating units 1703 and 1705; wavelength separating mirrors 1706 and 1709, a detecting unit 1704, and a computing unit 105. In the component concentration meter 900, an electromagnetic wave for detection 1701 oscillated by the oscillating unit 1703 and an electromagnetic wave for heating 1702 oscillated by the oscillating unit 1705 enter an aqueous solution 1708 containing ammonium ions and contained in a quartz cell 1707. The wavelength separating mirror 1706 that reflects the electromagnetic wave for heating 1702 and transmits the electromagnetic wave for detection 1701 is used. Thereby, the propagation path of the electromagnetic wave for heating 1702 and that of the electromagnetic wave for detection 1701 are overlaid within the aqueous solution 1708.

The electromagnetic wave for heating 1702 and electromagnetic wave for detection 1701 passed through the aqueous solution 1708 are separated by the wavelength separating mirror 1709 that reflects the electromagnetic wave for heating 1702 and transmits the electromagnetic wave for detection 1701 in the same manner. Only the electromagnetic wave for detection 1701 enters the detecting unit 1704, and the electromagnetic wave for detection 1701 that enters the detecting unit 1704 is monitored.

Here, the electromagnetic wave for heating 1702 is the ultraviolet light having a wavelength of approximately 190 nm, and the electromagnetic wave for detection 1701 is the near-infrared light having a wavelength of not less than 1100 nm and not more than 1180 nm or a wavelength of not less than 900 nm and not more than 990 nm.

The absorbance of the ultraviolet light having a wavelength of 190 nm in the aqueous solution containing ammonium ions is proportional to the concentration of ammonium ion. For this reason, the temperature of the propagation path of the electromagnetic wave for heating 1702 is more increased as the concentration of the ammonium ion is larger. In the near-infrared light having a wavelength of not less than 1100 nm and not more than 1180 nm or a wavelength of not less than 900 nm and not more than 990 nm, the absorbance by water changes proportional to the change in the temperature. For this reason, the temperature to be increased in the propagation path of the electromagnetic wave for heating 1702 can be determined from the transmittance of the electromagnetic wave for detection 1701.

Accordingly, the component concentration meter according to the present embodiment shown in FIG. 20 can determine the concentration of the ammonium ion contained in the aqueous solution 1708.

Here, in the present embodiment, the electromagnetic wave for detection is an electromagnetic wave having a wavelength at which the absorbance by other component than the target component changes according to the temperature of the object to be measured. Similarly to Embodiments 1 to 6, even if the electromagnetic wave for detection is an electromagnetic wave having a wavelength at which the absorbance by the target component does not change according to the temperature, the concentration of the component can be measured with accuracy as high as in Embodiments 1 to 6.

As described above, however, if the electromagnetic wave for detection is the electromagnetic wave having a wavelength at which the absorbance by the other component than the target component changes according to the temperature, the concentration of the component can be measured with higher accuracy in the case where there is no electromagnetic wave having a wavelength at which the absorbance by the target component itself changes according to the change in the temperature of the target component, and the case where the oscillating unit that generates an electromagnetic wave at such a wavelength is extremely expensive.

The same configuration can increase the accuracy in the measurement of the concentration of a variety of the target components in a variety of the objects to be measured. For example, the absorbance of the near-infrared light having a wavelength near 2257 nm is proportional to the concentration of a chloride ion. For this reason, if the near-infrared light having a wavelength near 2257 nm is used as the electromagnetic wave for heating, the concentration of the chloride ion can be measured with higher accuracy. Thereby, the concentration of sodium chloride contained in concrete and the like and causing salt damage can also be measured.

The absorbance of the near-infrared light having a wavelength near 1420 nm is proportional to the concentration of calcium hydroxide. Accordingly, if the near-infrared light having a wavelength near 1420 nm is used as the electromagnetic wave for heating, the concentration of calcium hydroxide can be measured with higher accuracy.

In the present embodiment, the configuration in which the concentration of the target component contained in the aqueous solution in the quartz cell is measured has been shown. The component concentration meter according to the present invention may be used as a water quality management system in water purifying plants or the like.

The same configuration can also determine the concentration of total cholesterols in the blood serum. Hereinafter, a method for measuring a concentration of the total cholesterols according to an oxygen method will be described.

First, using cholesterol esterase, esterified cholesterol contained in the blood serum is hydrolyzed into free cholesterol and fatty acid. Next, free cholesterol is reacted with cholesterol oxydase to produce hydrogen peroxide and Δ4-cholestenone. In the presence of peroxidase, the produced hydrogen peroxide is oxidatively condensed with 4-aminoantipyrine and phenol to produce a red quinone dye. This is placed into the quartz cell 1707 shown in FIG. 20 as the object to be measured.

In this case, desirably, the visible light having a wavelength of 450 to 670 nm is used as the electromagnetic wave for heating. Thereby, the concentration of the total cholesterols can be determined with high accuracy.

Desirably, good cholesterol (HDL) and neutral fat levels are determined in the same manner, and the concentration of bad cholesterol (LDL) is calculated by one of the following equations.

(1) In the case where the neutral fat level is not more than 400 mg/dl

LDL=total cholesterols−(HDL+neutral fat×0.2)

(2) In the case where the neutral fat level is more than 400 mg/dl

LDL=total cholesterols−(HDL+neutral fat×0.16)

If the LDL is calculated, a risk of arteriosclerosis can be measured more accurately.

If an arteriosclerosis index is calculated using the following equation, a risk of arteriosclerosis can be measured much more accurately.

Arteriosclerosis index=LDL÷HDL

Further, a combination of the device for measuring the concentration of cholesterol, the device for measuring a blood sugar level, and a device for measuring a blood pressure can provide a diagnosis apparatus that can determine metabolic syndrome. As the diagnosis reference, of three items of (1) blood serum dyslipidemia (neutral fat in the blood serum (triglyceride) of not less than 150 mg/dl or HDL cholesterol level of 40 mg/dl), (2) high blood pressure level (highest blood pressure of not less than 130 mmHg or lowest blood pressure of not less than 85 mmHg), (3) high blood sugar (fasting blood sugar of 110 mg/dl), the case where two or more can be found is diagnosed as the metabolic syndrome.

Besides calculation of the arteriosclerosis index or the example of diagnosis of the metabolic syndrome, by the health management system that measures the concentrations of a plurality of components in the human body to measure the health condition of the body from those values using the component concentration meter according to the present invention, the health condition can be measured more simply (at lower cost) and more accurately.

In the component concentration meter according to the present embodiment, similarly to Embodiments 1 to 7, more desirably, the transmittance of the electromagnetic wave for detection is measured several times at a different output of the electromagnetic wave for heating, and the transmittances in the respective cases are compared. This prevents the transmittance of the electromagnetic wave for detection from being reduced due to scattering, reflection, or absorption by other component than the target component in the object to be measured to cause measurement errors. Thereby, the concentration of the component can be measured with higher accuracy.

Similarly to Embodiments 3 to 5, the measurement of the concentration of the component using such a property that optical rotation or circular dichroism changes according to the change in the temperature may be used.

In the present embodiment, similarly to Embodiment 2, the concentration of the target component may be determined based on the transmittance of the electromagnetic wave for detection measured several times using the pump-probe method. Use of the pump-probe method enables the measurement of the concentration of the component based on the difference in the recovery rate of the absorbance from a supersaturated absorption state that is faster change of the optical property.

More desirable is the measurement of the concentration of the component using both of the change in the transmittance of the electromagnetic wave according to the change in the temperature and the recovery rate of the absorbance from the saturable absorption state. Thereby, a component concentration meter with higher accuracy can be provided.

As described above, the component concentration meter according to the present invention and the shipping inspection system and health management system using the component concentration meter have been shown. The configurations shown herein are only examples, and various modifications can be made without departing the scope of the present invention.

As described above, the component concentration meters according to the embodiments of the present invention have been described, but the present invention will not be limited to the embodiments.

Among a plurality of processors included in the component concentration meters according to the embodiments, at least part thereof is implemented as an integrated circuit LSI. Each of these processors may be formed into one chip, or part or all of the processors may be formed into one chip.

Integration of circuits is not limited to the LSI, and may be implemented as a dedicated circuit or a general-purpose processor. A FPGA (Field Programmable Gate Array) programmable after production of the LSI or a reconfigurable processor in which the connection and setting of the circuit cells within the LSI are reconfigurable may be used.

Part of the function of the component concentration meter according to the embodiment of the present invention may be implemented by a processor such as a CPU to execute a program. Further, the present invention may be the program, or a non-temporary computer readable recording medium having the program recorded. The program can be distributed through a transmitting medium such as the Internet.

Among the functions of the component concentration meters according to the embodiments and modifications thereof, at least part thereof may be combined. The numerals used in the description all are exemplified in order to specifically describe the present invention, and the present invention will not be limited to the numerals exemplified.

Without departing from the scope of the present invention, the present invention includes an embodiment with various modifications on Embodiments that are conceived by a person skilled in the art.

INDUSTRIAL APPLICABILITY

The component concentration meter according to the present invention can measure the target component contained in the object to be measured using the electromagnetic wave with high accuracy, can be used for the non-invasive analysis of the components in the living body such as glucose, protein, fat, moisture, and urea without extraction of the blood. Moreover, the inspection system can be provided in which the sweetness and sugar content of fruits and vegetables (particularly, fruits) before shipping, the concentration of the component contained in the test reagent, and the concentration of an object contained in an aqueous solution sample can be determined by a non-contact method.

REFERENCE SIGNS LIST 10, 100, 200, 300, 400, 500, 600, 700, 800, 900, 2001 Component concentration meter
20 Outputting unit
30, 104, 702, 1304, 1307, 1406, 1407, 1604, 1704, 1804 Detecting unit
40 Concentration determining unit
50, 102 Object to be measured
101, 1301, 1307, 1403, 1405, 1502, 1504, 1601, 1608, 1901 Electromagnetic wave
103, 302, 304, 1303, 1306, 1402, 1404, 1501, 1603, 1606, 1703, 1705, 1803 Oscillating unit
105 Computing unit
106 Filter
107 Depression projection smoothing material
108 Converging lens
301, 1702 Electromagnetic wave for heating
303, 1701 Electromagnetic wave for detection
701 Separating mirror
1302 Anterior aqueous humor in eye
1305 Crystalline lens
1308, 1409, 1411 Rotary polarized wave separator
1401, 1410, 1505 Dichroic mirror
1503 Wavelength converting unit
1602 Frozen mashed meat
1605, 1607 Optical fiber
1706, 1709 Wavelength separating mirror
1707 Quartz cell
1708 Aqueous solution (containing ammonium ion)
1801 Cup for irradiation with electromagnetic wave
1802 Calibration marking
1805 Protection solution
1806 Electromagnetic wave irradiating unit
1807 Electromagnetic wave detecting unit
1902 Cornea
1903 Iris
2000 Outgoing inspection system
2002 Conveyor belt

The invention claimed is:

1. A component concentration meter that measures a concentration of a target component contained in an object to be measured, the component concentration meter comprising:
an output unit configured to output an electromagnetic wave to the object to be measured;
a detecting unit configured to detect a property of the electromagnetic wave passed through the object to be measured under a first condition and under a second condition in which a temperature of the object to be measured is different; and
a concentration determining unit configured to determine the concentration of the target component contained in the object to be measured, based on (i) a property difference which is a difference between a property of the electromagnetic wave detected by said detecting unit under the first condition and a property of the electromagnetic wave detected by said detecting unit under the second condition, and (ii) a difference between the temperature of the object to be measured under the first condition and the temperature of the object to be measured under the second condition, wherein said output unit is configured to output an electromagnetic wave for detection that has a first wavelength and passes through the object to be measured to be detected by said detecting unit and to output an electromagnetic wave for heating that has a second wavelength and is absorbed by the object to be measured to increase the temperature of the object to be measured, wherein the electromagnetic wave for heating has an absorption by the object to be measured that is larger than an absorption of the electromagnetic wave for detection, and wherein the difference between the temperature of the object to be measured under the first condition and the temperature of the object to be measured under the second condition is caused by said output unit outputting the electromagnetic wave for heating to the object to be measured.

2. The component concentration meter according to claim 1, wherein the electromagnetic wave for detection has a property that significantly changes according to a change of the temperature of the object to be measured compared to the electromagnetic wave for heating.

3. The component concentration meter according to claim 1, wherein said detecting unit is configured to detect the property of the electromagnetic wave passed through the object to be measured under the first condition in which a first electromagnetic wave pulse is output from said output unit and under the second condition in which a second electromagnetic wave pulse having a different pulse energy from a pulse energy of the first electromagnetic wave pulse is output from said output unit.

4. The component concentration meter according to claim 3, wherein said output unit is configured to output the first and second electromagnetic wave pulses each having a different pulse energy by varying a peak power between the first and second electromagnetic wave pulses.

5. The component concentration meter according to claim 3, wherein said output unit is configured to output the first and second electromagnetic wave pulses each having a different pulse energy by varying an irradiation time between the first and second electromagnetic wave pulses.

6. The component concentration meter according to claim 1,
wherein the target component is glucose, and
wherein said output unit is configured to output the electromagnetic wave for detection having the first wavelength selected from (i) a range of not less than 1600 nm and not more than 1900 nm, (ii) a range of not less than 900 nm and not more than 1050 nm, or (iii) a range of not less than 1200 nm and not more than 1270 nm.

7. The component concentration meter according to claim 1,
wherein the object to be measured contains moisture, and
wherein said output unit is configured to output the electromagnetic wave for detection having the first wavelength selected from (i) a range of not less than 1100 nm and not more than 1180 nm or (ii) a range of not less than 900 nm and not more than 990 nm.

8. The component concentration meter according to claim 1,
wherein the object to be measured includes a biological cell, and
wherein said output unit is configured to output the electromagnetic wave for heating having a pulse width of not less than 10 ns and not more than 1 μs.

9. The component concentration meter according to claim 1,
wherein the object to be measured is an anterior aqueous humor in an eye,
wherein said component concentration meter further includes a cylindrical body having a bottom and an opening on a top surface of said cylindrical body, and holding a protection solution having a higher refractive index than a refractive index of the anterior aqueous humor in the eye within the cylindrical body having the bottom,
wherein said output unit is provided on a side surface of said cylindrical body having the bottom so as to output an electromagnetic wave passing through the protection solution to the opening, and
wherein said detecting unit is provided on the side surface of said cylindrical body having the bottom so as to detect a property of the electromagnetic wave that enters from the opening and passes through the protection solution.

10. The component concentration meter according to claim 9, wherein the surface of said cylindrical body having the bottom is light-shielded.

11. The component concentration meter according to claim 1, further comprising an electromagnetic wave converging unit configured to converge the electromagnetic wave output from said output unit, and provided in an electromagnetic wave propagation path between said output unit and the object to be measured.

12. The component concentration meter according to claim 1, further comprising a storing unit configured to store an association table that holds the property difference, the difference in the temperature, and the concentration of the target component in association,
wherein said concentration determining unit is configured to determine the concentration of the target component corresponding to the property difference and the difference in the temperature detected by said detecting unit with reference to the association table held in said storing unit.

13. The component concentration meter according to claim 1, further comprising a smoothing material that smoothes depressions and projections of the object to be measured in order to provide a uniform distribution of intensity of an electromagnetic wave in a propagation path from said output unit to said detecting unit.

14. The component concentration meter according to claim 1, comprising a polarized wave separating unit configured to extract a predetermined polarization component contained in the electromagnetic wave passed through the object to be measured,
wherein said detecting unit is configured to detect a degree of optical rotation of the polarization component extracted by said polarized wave separating unit under the first condition and under the second condition, and
wherein said concentration determining unit is configured to determine the concentration of the target component contained in the object to be measured, based on the difference in the temperature and a difference in the degree of optical rotation.

15. The component concentration meter according to claim 1,
wherein said output unit is configured to output an electromagnetic wave having a first wavelength and an electromagnetic wave having a second wavelength, and wherein said component concentration meter further comprises:
   a synthesizing unit configured to synthesize the electromagnetic wave having the first wavelength with the electromagnetic wave having the second wavelength and to output the synthesized electromagnetic wave to the object to be measured; and
   a separating unit configured to separate the electromagnetic wave passed through the object to be measured into the electromagnetic wave having the first wavelength and the electromagnetic wave having the second wavelength.

16. The component concentration meter according to claim 1, wherein said output unit includes:
   an oscillating unit configured to oscillate an electromagnetic wave having a first wavelength; and
   a wavelength converting unit configured to convert part of the electromagnetic wave oscillated by said oscillating unit into an electromagnetic wave having a second wavelength that is different from the first wavelength.

17. A component concentration measurement method that measures a concentration of a target component contained in an object to be measured, the component concentration measurement method comprising:
   outputting an electromagnetic wave to the object to be measured;
   detecting a property of the electromagnetic wave passed through the object to be measured under a first condition and under a second condition in which a temperature of the object to be measured is different; and
   determining the concentration of the target component contained in the object to be measured, based on (i) a property difference which is a difference between a property of the electromagnetic wave detected in said detecting under the first condition and a property of the electromagnetic wave detected in said detecting under the second condition, and (ii) a difference between the temperature of the object to be measured under the first condition and the temperature of the object to be measured under the second condition, wherein said outputting further outputs an electromagnetic wave for detection that has a first wavelength and passes through the object to be measured to be detected by said detecting and outputs an electromagnetic wave for heating that has a second wavelength and is absorbed by the object to be measured to increase the temperature of the object to be measured, wherein the electromagnetic wave for heating has an absorption by the object to be measured that is larger than an absorption of the electromagnetic wave for detection, and wherein the difference between the temperature of the object to be measured under the first condition and the temperature of the object to be measured under the second condition is caused by said outputting performing the outputting of the electromagnetic wave for heating to the object to be measured.

* * * * *